United States Patent [19]

Serfontein

[11] Patent Number: 5,631,271
[45] Date of Patent: May 20, 1997

[54] METHODS AND PREPARATIONS FOR THE TREATMENT AND PROPHYLAXIS OF METABOLIC DISTURBANCES

[76] Inventor: Willem J. Serfontein, 47 Selikats Village, Selikats Causeway, Faerie Glen, South Africa, 0043

[21] Appl. No.: 100,433

[22] Filed: Aug. 2, 1993

Related U.S. Application Data

[63] Continuation-in-part of Ser. No. 466,676, Jan. 17, 1990, Pat. No. 5,254,572, which is a continuation-in-part of Ser. No. 125,996, Nov. 27, 1987, abandoned, and Ser. No. 395,033, Aug. 17, 1989, abandoned, which is a continuation-in-part of Ser. No. 125,996, which is a continuation-in-part of Ser. No. 153,973, Feb. 9, 1988, abandoned.

[30] Foreign Application Priority Data

Jan. 17, 1989 [GB] United Kingdom ............... 8900924
Nov. 29, 1986 [ZA] South Africa ................... 86/4001
Sep. 14, 1992 [ZA] South Africa ................... 92/6989

[51] Int. Cl.$^6$ ................................................ A61K 31/44
[52] U.S. Cl. .......................................... 514/345; 514/351
[58] Field of Search ................................ 514/345, 351

[56] References Cited

U.S. PATENT DOCUMENTS 5,254,572  10/1993  Serfontein ............................. 514/345

OTHER PUBLICATIONS

Dialog File 446, 001148023, 1962.
Dialog File 446, 01238461, 1968.
L. Brattstrom, et al. Atherosclerosis 81 (1990) 51–60.
L. Brattstrom, et al. Scand J Clin Lab Invest 1988: 48215–211.
AJ Olszewski, et al., Atherosclerosis, 75 (1989) 1–6.

Primary Examiner—Shailendra Kumar
Attorney, Agent, or Firm—Omri M. Behr, Esq.

[57] ABSTRACT

Treatment or prophylaxis of depressed or inadequate intracellular pyridoxal phosphate levels in a human or animal patient resulting from a condition, wherein the pyridoxine (PN)—pyridoxal phosphate (PLP) pathway is disturbed by cellular defects and concomitant enzyme deficiencies. These may be due to genetic causes or cell immaturity, as occurs in infants and in diseases resulting in erythrocytes destruction. In infants it was found, for the first time, that this leads to elevated homocysteine levels.

The deficiencies are counteracted by the administration of pyridoxal or a precursor of pyridoxal which in vivo, once it has entered the bloodstream, is rapidly convened into pyridoxal without the intervention of oxidase or oxygen, optionally and preferably without the intervention of kinase and/or of PN in slow-release form and at a daily dosage rate not exceeding 0.7 mg/kg/day in the long term.

In the case of pharmaceutical or dietary preparations for infants, in particular premature infants, these contain in addition vitamin B12 and folic acid or folate.

43 Claims, No Drawings

METHODS AND PREPARATIONS FOR THE TREATMENT AND PROPHYLAXIS OF METABOLIC DISTURBANCES

RELATED APPLICATIONS

This is a continuation in part of allowed Ser. No. 07/466,676 dated Jan. 17, 1990, now U.S. Pat. No. 5,254,572, which in turn is a continuation in part of Ser. No. 07/125,996, dated Nov. 27, 1987 (now abandoned) and of Ser. No. 07/395,033 dated Aug. 17, 1989 now abandoned, which is likewise a continuation in part of Ser. No. 07/125,996 now abandoned and which is also a continuation in part of Ser. No. 07/153,973 dated Feb. 9, 1988, now abandoned.

The contents of the said allowed application Ser. No. 07/466,767 are incorporated herein by reference. Likewise the evidence filed in the parent applications is specifically cross-referred to herein as part of the present disclosure and so are the contents of all priority documents filed with the present or any of the aforesaid earlier applications.

The disclosure of applicant's copending application entitled "Pharmaceutical preparations for lowering homocysteine levels" claiming the priority of South African patent application 92/6990, dated 14 Sep., 1992 is also specifically cross-referred to herein, together with the contents of its priority document, as part of the present disclosure.

The same applies to the copending CIP of the parent application (now allowed) entitled "Method and preparation for counteracting PN-PLP pathway disturbances caused by vitamin B6 antagonists".

FIELD OF THE INVENTION AND BACKGROUND

The present invention, according to a specific aspect thereof, relates to pharmaceutical, veterinary or dietary compositions and the use thereof for a method of treatment or prophylaxis of depressed or inadequate intracellular pyridoxal phosphate levels in a human or animal patient resulting from a condition, wherein the pyridoxine (PN)—intracellular pyridoxal phosphate (PLP) pathway is disturbed or insufficient. The invention can make use of new diagnostic methods and means for diagnosing such depressed or inadequate pyridoxal phosphate levels or disturbance in the pathway, more particularly for use in conjunction with the said treatment or prophylaxis. More particularly, according to one aspect, the invention relates to that genus of the aforegoing compositions and methods, where the said disturbance of the pathway is due to an inherent cellular defect, e.g. caused by genetic oxidase polymorphism or immaturity of cells, resulting in deficient oxidase activity. The condition can be aggravated by chemical substances which are vitamin B6 antagonistic. Such substances can be biogenic. They can be toxins, e.g. of microbal origin, or toxic substances to which the body was exposed accidentally, but the invention has particular application to counteracting side-effects of a variety of pharmaceuticals which are vitamin B6 antagonists and which may be used to combat diseases which lead to the aforesaid cellular defects.

The invention is particularly concerned with insufficiencies in the aforesaid pathway due to cellular immaturity causing depressed activity of oxidase enzymes.

The present invention, according to a specific aspect, relates to compositions for the treatment and prophylaxis of metabolic disturbances in infants, more particularly of elevated homocysteine and/or methionine levels in the blood of infants and pathological disturbances connected therewith.

The relationship between even moderately elevated blood homocysteine levels homocysteineaemia and various pathological conditions, in particular vascular and neurological diseases has been firmly established in adults. (Ueland et al, Scan. Clin. Lab. Invest. 1988, 48:215)

Hitherto, this problem was considered to primarily affect adults and possibly adolescents, since it was primarily believe to be connected with long term dietary factors, possibly enhanced by genetic factors.

It therefore came as a great surprise, when the present applicant conducted homocysteine measurements in the serum of new born and premature infants (something which had never before been reported) and discovered an amazing frequently of homocysteine abnormalities in such infants in addition to a number of important additional findings.

It was found that average homocysteine levels in healthy infants (6–7 $\mu mole/l$) are much lower than in adults (for whom up to 16.3 $\mu mole/l$ is normal). However, surprisingly a relatively large proportion of infants were found to have relatively elevated homocysteine levels. Based on experiments conducted by the applicant on adults and various blood measurements carried out on the infants, it was possible to reach conclusions as to causes and potential consequences, and the present invention proposes appropriate countermeasures.

It was found that in ideal circumstances healthy infants, from healthy mothers and wholly breast fed are protected naturally against elevated homocysteine levels, a fact which indirectly confirms the danger residing in homocysteine. In healthy new-born infants plasma levels of pyridoxal, vitamin B12 and folate were found to be considerably higher than in adults. Applicant has established that these high levels provide a natural protective mechanism against accumulation of toxic homocysteine levels.

It was possible to correlate deficiencies in respect of one or more of the aforegoing with elevated homocysteine levels in the respective infants and detect connections with genetic factors, with pre-natal and post-natal maternal nutritional status (the latter being relevant to breast fed infants). However, most alarming of all was the discovery of the extent to which these elevated homocysteine levels can be ascribed to bottle feeding with non-human milk and milk formulae based on cow's milk. A careful assessment of certain differences between human and non-human milk has revealed plausible causes for the prevalence of homocysteineaemia amongst infants. In particular, cow's milk contains 4 times more methionine than mother's milk yet is lacking proportionally in factors which would prevent or counteract the transformation of this excessive amount of methionine into homocysteine.

Fraying and splitting of the vascular internal elastic membranes has been observed as a clinical symptom of elevated homocysteine levels in adults. This same symptom was described by Jaffe in 176 babies who had died of different causes during their first 3 months of life. Sudden infant death syndrome has been found to be particularly common amongst bottle-fed babies.

The vascular damage caused by homocysteine is well established. Research has shown that this kind of damage is the primary cause of and precondition for subsequent vascular damage by cholesterol. Research has further revealed that cholesterol only becomes dangerous once it has been oxidised to oxycholesterol, either in the diet or in vivo. This is brought about by the intervention of free radicals. In this context it is particularly alarming that homocysteine itself is a known stimulant for free radical induced oxidation of lipoproteins, including that of cholesterol-rich lipoproteins, this besides other harmful effects of free radicals in vivo. Moreover, in a manner to be explained further below, thermally processed bottle feed products are themselves rich in oxycholesterol but are deficient in counteracting substances present in human milk, Even if the adverse factors described above, in particular elevated homocysteine result in no immediately apparent symptoms, they may predispose to atherosclerosis in later life.

The damage caused by homocysteine in infants is obviously not limited to the vascular system but may include many other tissues and systems including the central nervous system, which is particularly vulnerable at this stage.

The invention is inter alia based on the discovery of the above described hitherto unknown problem and seeks solutions to this and/or related problems.

The present invention is based on extensive research which has brought to light a large number of clinical or pathological conditions in animals or man associated with depressed or inadequate intracellular pyridoxal phosphate levels, resulting from factors whereby the pyridoxine-pyridoxal phosphate pathway is disturbed or rendered insufficient.

DISCUSSION OF PRIOR ART

The vital role of vitamin B6 (hereinafter abbreviated to B6) in health and disease has been extensively researched over the past two decades. It is now realised that many serious diseases and clinical conditions are associated with reduced blood and cellular vitamin B6 activity. However, until now many of the physiological interrelationships in animals and humans have not been known or understood. In particular there has been confusion as to whether observations relating to vitamin B6 and B6 vitamin deficiencies were results of clinical conditions or whether these deficiencies were causally related to the clinical conditions. This was due inter alia to a disregard of certain aspects of the pharmacokinetics involved, and of the role of different B6 vitamins. Prior to the present invention certain of these vitamins had never been determined systematically in biological fluids during disease processes, and indeed no suitable routine methods had existed for such systematic determinations.

It is known that vitamin B6 occurs in three primary forms, known by their trivial names: namely the nonphosphorylated vitamins pyridoxine (PN, formula I), pyridoxal (PL, formula II) and pyridoxamine (PM, formula III), as well as the corresponding phosphorylated forms PNP, PLP and PMP. Of these, PN or its acid addition salts, e.g. the hydrochloride is the form exclusively used commercially in pharmaceutical formulations up till now. It is also the main B6 vitamin in plants.

Inside living human and animal cells, PLP is the biologically active form of vitamin B6, acting as co-enzyme in more than 100 biological reactions. Pharmaceutical compositions for the aforesaid purposes, comprising B6 in the form of PL had not been commercially available previously. In fact, there has been a distinct prejudice in the art against the administration of B6 in any form other than that of PN. That prejudice was based not only on cost but also on the relative stability and longer shelf-life of PN. In vitro PL is less stable. In short, there existed and still exists a severe prejudice in the art against the use of B6 vitamins other than the conventional PN such that persons skilled in the art were disinclined to accept that such other vitamins could offer any worthwhile advantages.

Occasionally the prior art patent literature does refer to some or all six of the aforesaid B6 vitamins in various pharmaceutical uses and compositions. However, as a rule, PN is the vitamin emphasized in the disclosure of specific embodiments. In general, these disclosures do not offer any inducement or reason why preference should be given to these other vitamins rather than the more common and readily available PN. The use of PL is disclosed in Examples 6 and 7 of GB Patent specification 1 201 014 (Merck AG) as part of a multivitamin preparation. No reasons are given for that choice, nor is the daily dosage rate disclosed.

French patent specification 50 871 teaches compositions specifically for cardiac complaints comprising a combination of two active ingredients one being theophylline or one of certain derivatives thereof or camphor derivatives or digitalis and the other being vitamin B6. Although the specification states that vitamin B6 can be employed in the form of any of its aforesaid vitamins, the enabling disclosure, in particular that of the examples, is restricted to pyridoxine. No explanation is given of the therapeutic mechanism. Indeed the rationale behind the teachings of the reference is obscure, because it is said that the vitamin B6 as such has no effect on cardiac function. No teachings relating to the purposes and therapeutic effects contemplated by the present invention can be extracted from that French patent when read in the light of the knowledge in the art at the time. In particular the French patent does not teach the administration of vitamin B6 for the treatment or prophylaxis of actually depressed or inadequate intracellular PLP levels. Disturbances of the PN-PLP pathway are neither referred to nor suggested.

Surprisingly the conventional manners of administration of PN frequently do not lead to the desired alleviation of B6 deficiencies in blood plasma and in living cells, inter alia in critically ill patients. The consequences of such deficiencies can be most severe. Neither the extent of these consequences

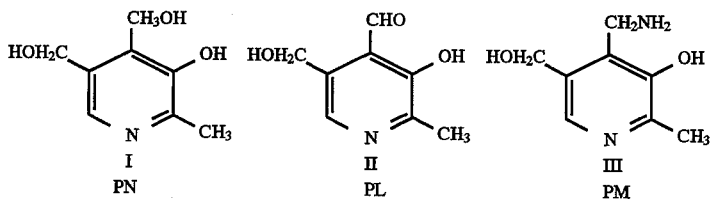

Inside living human and animal cells, PLP is the biologically active form of B6 nor the causes thereof had been appreciated in the past, or adequately so. As will be explained further below, these B6 deficiencies are on the one hand caused or aggravated by a variety of physiological factors. They are in turn themselves the cause of a breakdown of vital physiological functions, which is often fatal. Many important drugs used in the treatment of diseases, whilst combatting the primary symptoms and/or causes of such diseases, have now been identified as severe contributors to B6 deficiencies which have unwittingly aggravated this breakdown of physiological functions. The administration of PN in the prior art manner at best achieves partial and relatively slow alleviation of the B6 deficiency, and often not at all, particularly in the severely ill patient. Contrary to prior art beliefs the problem cannot be overcome by increasing the dosage of PN for reasons now established for the first time by us and explained in greater detail below.

A recent German application (P 37 05 549.6) having a date later than that of the parent application hereof teaches the use of pyridoxal, pyridoxamine and their phosphates for the regulation of cholesterol levels and lipid compositions in serum. The specification contains no teachings pertaining to the uses herein contemplated and no teachings relating to the further disclosure added in the present CIP.

Masons et al, Brit. Med. J. (1973), 1, 389–390, report successful treatments of acquired sideroplastic anaemia with intramuscular pyridoxal-5-phosphate (PLP) in cases which did not respond to PN. It was not realised that, as taught by the present invention, the administration of unphosphorylated PL, even by the oral route, would have been preferable and would have eliminated a further potential bottleneck in the metabolic pathway.

Pharmaceutical preparations containing a) vitamin B6, b) folate and e) vitamin B12 have been described, albeit for totally different purposes and mostly in ratios differing from the ratios or at least from the preferred or more preferred ratios which are taught by the present invention. In GB-PS 1201 014 (Examples 6 and 7) the ratio of a):b)=3:1 and that of b):e)=1000:5. No indication is disclosed for these dosages which, however, are clearly not intended for paediatric use. GB-PS 2254 556, published after the priority date of the present disclosure also discloses compositions, only some of which contain in combination folic acid, vitamin B12 and vitamin B6. No distinction is drawn between pyridoxine, pyridoxal and pyridoxamine. These compositions are intended for adolescent girls. GB-PS 149 3993 discloses compositions for healing obesity. Pyridoxal is not disclosed. GB-PS 2197 587 describes a "blood conditioning tonic" for race horses. Pyridoxal is not disclosed. GB-PS 1431 841 discloses preparations for cataract treatment. The ratios are different from those according to the invention and pyridoxal is not disclosed. GB 101 3939 discloses compositions for paediatric purposes in ratios which overlap the broadest ratio according to the invention, but the important feature that the vitamin B6 must be in the form of pyridoxal or suitable precursor thereof is not disclosed. This also applies to EP-0144051, EP 0121 036 or PCT WO 83/00085.

Not one of the aforesaid references discloses such combinations for the treatment or prophylaxis of elevated homocysteine levels in infants, or the crucial role of pyridoxal in that context.

OBJECTS OF THE INVENTION

It is an object of the invention to provide a method and means for the treatment or prophylaxis of depressed intracellular PLP levels in humans and animals resulting from a disturbance of the PN- plasma PL- intracellular PLP pathway in the body due to an inherent cellular defect, e.g. caused by genetic oxidase polymorphism or immaturity of cells resulting in deficient oxidase activity.

It is a further object to provide nutritional supplementation for infants.

It is a further object to provide a method and means for the treatment and prophylaxis of elevated homocysteine and/or methionine levels in infants and of clinical conditions associated with such levels.

GENERAL DESCRIPTION OF THE INVENTION

The present invention according to one aspect thereof provides a new method of treatment. According to a further aspect it provides new pharmaceutical or dietary compositions as well as combinations thereof with other drugs. According to yet another aspect the invention combines the method with certain diagnostic tests and provides the diagnostic means (more particularly in kit form) for carrying out those diagnostic tests, as disclosed in the parent patent.

The compositions according to the invention are generally supplied with appropriate instructions for carrying out the method (treatment or prophylaxis) as set out above. Such instructions may be oral but are preferably in written, printed or pictorial form, e.g. included in or applied to a package containing the compositions. Packages may take the form of dispensors, designed to prescribe to the patient a particular dosage regimen.

The present invention is based on the surprising finding that substantially improved and more rapid alleviation of B6 deficiency can be attained by administering to the patient an effective mount of a pharmaceutical or dietary Composition, comprising as an active ingredient pyridoxal (PL) itself or a precursor of pyridoxal which in vivo, once it has entered the bloodstream, is rapidly converted into pyridoxal without the intervention of oxidase or oxygen, optionally with a stabiliser or antioxidant and/or a potentiator for the pyridoxal. Preferably the precursor of pyridoxal is one which is also rapidly converted as aforesaid without the intervention of kinase. In other words, this preferred feature excludes the phosphorylated forms.

Pharmaceutical compositions comprising vitamin B6 for that purpose in the form of PL or said precursor have not been proposed or been available previously. In fact, there has been a distinct prejudice in the art against the administration of B6 in any form other than that of PN. That prejudice was based not only on cost but also on the relative stability and long shelf-life of PN. In vitro PL is far less stable. The art took no or insufficient cognizance of the fact that PN has an extremely short half-life in blood in vivo, that it is readily excreted and/or converted into physiologically unavailable compounds, and that PN must pass through a chain of biochemical reactions before it can enter the cells and finally end up there as required in the form of active vitamin B6, i.e. pyridoxal phosphate (PLP) and that this chain of reactions can be compromised at various stages, in different clinical situations.

Various facts are known, mostly in isolation, concerning B6, its occurrence and biochemistry. However, this knowledge has not been properly correlated, nor could the conclusions be drawn on which the present invention is based.

The present invention is based on the applicant's own, new experimental findings, including the pharmacokinetics of B6 vitamins in humans, a new interpretation of aspects of the biochemistry of B6 made possible by these experimental findings, as well as new concepts based on the results of our experiments throwing new light on various biochemical observations which previously were not understood or correlated. This has been made possible by our development for the first time of a practical method of determining PL in body fluids in the clinical situation.

The method according to the invention is applied to a variety of types of clinical situations, all involving the said depressed or inadequate intra cellular PLP levels, however, the following description will show that many, if not most clinical or pathological conditions fall into two or more of those types.

One type of such situations comprises conditions involving depressed cell oxygenation, depressed oxidase activity and/or depressed kinase activity. Depressed cell oxygenation (socalled anaerobic condition) is a common feature of many serious diseases. Depressed oxidase activity can be chemically induced by diseases or drugs or can be due to an enzymatic cellular defect. The present invention is concerned with the latter, which may, however, be aggravated by chemical pyridoxal phosphate depletion in cells, as dealt with more fully in the aforesaid copending CIP of the parent application of the present patent application.

This includes treatment of a patient suffering from a genetic lack of oxidase or genetic oxidase polymorphism.

It also includes the treatment of a condition wherein the depressed or absent enzymatic activity is caused by cellular immaturity. This in turn includes the treatment of infants suffering from intracellular pyridoxal phosphate insufficiency, in particular the treatment of premature infants.

A particular group of situations involves the treatment of a condition involving a depressed level of enzymatically mature or intact erythrocytes and/or lack of haemoglobin, e.g. as may occur in some forms of anaemia or in a patient suffering from a microbial disease involving destruction of erythrocytes. Such disease usually in addition causes the release of toxins or biogenic polyamines.

The invention also provides that the disturbance of the pathway is measured and the effective amount of composition is administered in accordance with the degree of disturbance measured. e.g. by measuring the oxidase activity in a cell sample, e.g. as disclosed in the now allowed parent application, now U.S. Pat. No. 5,254,572.

According to the invention the pyridoxal or precursor is administered at a daily dosage rate, calculated on the basis of pyridoxal of 0.01 to 4.3 mg/kg bodyweight intravenously, or 0.04 to 5.7 mg/kg bodyweight intramuscularly or 0.04 to 7.2 mg/kg bodyweight subcutaneously, or 0.03 to 7.2 mg/kg bodyweight orally. Compositions according to the invention are formulated accordingly. Preferably the dosage rate is 0.07 to 2.2 mg/kg intravenously or 0.07 to 2.9 mg/kg intramuscularly or subcutaneously or 0.07 to 3.6 mg/kg orally.

In addition zinc and/or magnesium may be provided as a potentiator for pyridoxal at a dosage rate of 0.05 to 0.9 mg/kg/day of zinc and 0.5 to 10 mg/kg/day of magnesium. Particularly, where anaerobic intracellular conditions are to be treated, glutamate may serve as a potentiator, e.g. at a dosage rate of 0.04 to 20 mg/kg/day.

For reasons still to be explained below the invention produces maximum benefits if the composition according to the invention is provided as an infusion or in another sustained, continuous release galenic form.

In some embodiments for the treatment of infants, e.g. premature infants the dosage rate calculated as pyridoxal is 0.01 to 1.0 mg/kg bodyweight per day intravenously, 0.017 to 2.0 mg/kg bodyweight per day intramuscularly or subcutaneously or 0.008 to 1.0 mg/kg bodyweight per day orally. Here as well the composition may be administered as an infusion. In addition or in the alternative the composition is added in the form of a nutritional supplement in dosage units to a feed formulation or the composition is itself an infant formulation containing the said pyridoxal or precursor in the required concentration for oral administration.

The aforegoing teachings applicable to the method apply analogously to the galenic forms and dosage units in which compositions according to the invention are presented.

In dietary compositions the pyridoxal or precursor becomes partly absorbed in the components of the diet resulting in a degree of slow, sustained continuous release effect. If the composition is presented as an infusion, that effect results from the manner of administration. Galenic forms of presentation are preferably galenically formulated for infusion or for another form of sustained, continuous release of pyridoxal or said precursor to the patient. Because of the mechanisms involved in the use of the invention, it is particularly important for maximum beneficial effects that the relatively low concentrations of pyridoxal are made available to the body continuously over a prolonged period, as evenly as possible.

According to certain embodiments, the composition comprises PL or a physiologically compatible acid addition salt or complex of PL which in vivo rapidly releases PL, or a mixture composed of two or more of these as the only source or sources of vitamin B6.

To protect against aerial oxidation, the composition (whether provided in solution form or as a solid, e.g. a powder) preferably contains an antioxidant, for example ascorbic acid (or a physiologically compatible salt thereof), the latter, for example, in a concentration of from 1 to 5000 mg per liter, preferably 50–500 mg per liter, e.g. 100 mg per liter, the concentrations given referring to a composition in the form of a parenteral solution, e.g. an infusion solution or to the required antioxidant content of a composition provided in the form of a powder to yield the stated concentration in an infusion solution, prepared therefrom. Even near the lower limit, ascorbic acid is effective as an antioxidant. However, in the higher concentrations, ascorbic acid also becomes effective physiologically as a source of vitamin C which is often desirable, e.g. in infusion solutions. An alternative or additional antioxidant may be sodium metabisulphite or any other compatible biological antioxidant.

Although PL is readily resorbed when administered for example per os, some preferred embodiments, particularly for emergency use, are in a form adapted for or readily adaptable for parenteral administration, preferably intravenous administration and in particular in a form adapted for or readily adapted for intravenous infusion. The latter embodiments may contain the conventional ingredients of an infusion solution, for example electrolytes, glucose and/or conventional extenders, excipients and the like. Since B6 in the form of PL in solution has a limited shelf-life, the composition may alternatively be provided in the form of a dry powder, preferably vacuum-packed in dark-coloured ampoules, the dry powder containing all the required additives to permit immediate use of the composition as an infusion solution after dissolution in, and suitable dilution to the required concentration with, sterile water. Alternatively, the powdered form of the pharmaceutical composition may be adapted such that it may be dissolved in any other standard infusion solution used under these circumstances.

As a further alternative the composition in powder form may be separately made up with sterile water and mixed with any other standard infusion solution before use; or said solution of the composition may be made up separately and administered together with a standard infusion solution after mixing in the feed tube of the infusion apparatus according to known art.

Preferred embodiments of the composition comprise as a further ingredient or ingredients one or more of the substances: glutamate, riboflavine, and physiologically compatible salts of zinc and magnesium.

Riboflavine, zinc ions and magnesium ions are co-factors in the enzymatic conversion of PN into PL, and zinc ions and magnesium ions are also co-factors in the phosphorylation of the vitamins PN and PL. Therefore these substances augment the conversion of PN when administered as part of the composition or separately, e.g. with the diet, even in patients suffering from reduced liver function to make more PL available to the body, and thereby augment the administration of PL in accordance with the present invention. Furthermore, as explained later in this specification, efficient glycolysis during ischaemia, e.g. in a coronary heart patient, is not only dependent on functionally available intracellular PLP, the phosphorylated form of PL (which according to the invention is supplemented by intravenous administration of a PL-containing infusion solution), but the action of the PLP during the critical period following a myocardial infarction (MI) incident is assisted by the provision of supplementary glutamate. Similar benefits arise from glutamate supplementation in other cells.

Sometimes it is desirable to include in the composition in addition pyridoxine or pyridoxine phosphate or a pharmaceutically acceptable complex or acid addition salt thereof, and in such cases in particular it is preferred to include riboflavin as a cofactor or potentiator for pyridoxine in an mount adapted to provide an effective dosage rate of 0.05 to 0.2 mg/kg/day, for example. This applies particularly to infant feed formulae and supplements or feed additives, where it is desirable to stimulate the enzyme system of the immature cells so as to develop its normal ability to convert PN into intracellular PLP.

Certain embodiments of infant feed formulae or additives or nutritional supplements for such formulae will generally comprise pyridoxal or said precursor in such concentration that the daily intake will be in the range 0.008 to 1.0 mg/kg bodyweight of pyridoxal. More particularly the said concentration is such that the daily intake of pyridoxal will be in the range 0.06 to 0.16 mg/kg. In the case of an additive or nutritional supplement, this is preferably in dosage units containing pyridoxal or said precursor in such concentration that the daily intake is distributed over from 1 to 6 dosage units. For example, such composition is in the form of solid dosage units formulated for a daily intake equivalent to from 0.008 to 0.8 mg/kg bodyweight pyridoxal or pyridoxamine or from 0.013 to 1.2 mg/kg bodyweight of pyridoxal phosphate or pyridoxamine phosphate, or a mixture of the aforegoing, wherein the said intake is divided pro ram. The phosphates are used in such somewhat higher concentration to allow for losses during the conversion into PL. The preferred infant formula or nutritional supplement or additive in addition contains pyridoxine or a complex or acid addition salt of pyridoxine in a concentration adapted to provide a daily intake of pyridoxine of 0.007 to 1.0 mg/kg bodyweight and preferably in addition contains riboflavin in a concentration adapted to provide a daily intake of 0.05 to 0.2 mg/kg bodyweight.

Of particular importance in the context of intracellular enzymatic insufficiencies involving the PN-PLP pathway are compositions according to the invention for use in the treatment or management of a condition involving microbial infection causing erythrocyte destruction, e.g. for use in the treatment or management of malaria, Bartellosis, Rift Valley fever, corridor disease or biliary fever. These may be used or formulated in combination with a drug for combating the microbial infection in a common package or in a common dosage form.

It will be understood from the principles underlying the present invention, that compositions in accordance with the invention may be provided with great advantage in the form of a blood supplement or substitute or blood transfusion compositon or an additive for addition to any of the aforegoing.

1. The crucial parameter which determines the vitamin B6 status of a patient is the intracellular level of PLP. Plasma PLP determinations can be very misleading, because it is possible for intracellular PLP levels to be dangerously depressed in spite of apparently satisfactory plasma PLP levels.
2. The capacity of the body to convert PN into intracellular PLP is limited and vitamin B6 antagonists tend to create bottlenecks in this pathway which cannot be overcome by the prior art excessive dosages of PN (or PNP).
3. Attempts to restore a healthy intracellular PLP status by high dosage rates of PN (or PNP), particularly when administered in bolus form, are in fact counterproductive. Exceeding the capacity of the body to utilise PN (a capacity which may be depressed not only by the vitamin B6 antagonists but also by ancilliary factors, e.g. liver damage, genetic factors) can actually aggravate the depressed intracellular PLP status, resulting in PN-toxicity symptoms very similar to those of a vitamin B6 deficiency.

An aspect of the invention which has emerged as one of particular importance is that which follows and which is concerned with counteracting elevated homocysteine and/or methionine levels in the blood of infants.

Thus, the present invention provides a new use of the substances hereinafter set out for the manufacture of a new pharmaceutical or dietary preparation for the treatment or prophylaxis of elevated homocysteine and/or methionine levels in the blood of human infants and pathological disturbances connected therewith, said preparation comprising in combination:

a) vitamin B 6 as such or in the form of a pharmaceutically acceptable acid salt, at least in part in the form of pyridoxal (PL) or a compound which in vivo readily releases PL without the intervention of oxidase enzyme or oxygen.

b) folate or a precursor of folate which releases folate in vivo, and c) vitamin B12, with or without intrinsic factor, in the following ratios:

| a):b) | from 1:25 | to 10000:1 |
|---|---|---|
| preferably | from 2:5 | to 150:1 |
| more preferably e.g. 15:2, and | from 13:1 | to 100:1 |
| b):c) | from 1:1 | to 50000:1 |
| preferably | from 2:1 | to 4000:1 |
| more preferably e.g. 400:11 | from 10:1 | to 1000:1 |

The preparation for the treatment or prophylaxis of elevated homocysteine and/or methionine levels in the blood of infants and pathological disturbances connected therewith.

The preparation in accordance with the invention can be galenically prepared for parenteral administration, e.g. by infusion. However, the preferred dosage forms are for oral use.

It is very important for optimum effects for the daily dosage to be spread as evenly as possible over a 24 hour period. This is best achieved in the case of oral administration, if the preparation is administered regularly at feeding times, e.g. as part of a bottle-feeding programme. For that purpose the preparation may take the form of paediatric drops or of dosage units such as soluble tablets, rapidly disintegrating tablets—or powders or granulates prepacked into sachets. Powders or granulates may also be provided with a measuring spoon or scoop for determining the desired dose.

The composition may also be incorporated in a bottle-feed powdered milk formula.

It has surprisingly been found that PL serum levels in healthy new-born babies are very much elevated, thus underlining the importance of PL in the metabolism of infants. This is in line with the fact that human milk in contrast to cow's milk or goat's milk has a high PL content and little or no PN content. New-born infants, particularly when premature, are enzymatically poorly equipped to convert pyridoxine (P1ND, the conventional source of vitamin B6 in non-human milk and conventional infant milk formulae, into the required PL. The present invention now provides a new and pressing reason for the need in infants to supplement plasma PL. Plasma PL is the only form of vitamin B6 capable of entering most cells in humans through the cellular membranes, in order to be immediately converted into intracellular pyridoxal phosphate (PLP), the only active form of vitamin B6 in humans. Also the PL form of vitamin B6 is the form needed as a co-factor for the enzyme cystathione synthase, which serves to convert homocysteine into cysteine by the transsulfuration pathway. This reaction reduces the methionine pool in the body and is accordingly important to limit the re-formation of homocysteine. Infants deficient in plasma PL lack the ability to degrade homocysteine, which may then lead to homocysteineaemia.

Prior art attempts at counteracting PL deficiency in infants by high dosage rates of PN, particularly when in bolus form, can be dangerous and result in toxicity effects similar to those of a depressed vitamin B6 status. As more fully explained in the aforesaid parent application, this is due to competitive inhibition of the PN-PLP (intracellular) pathway by excessive supplies of PN.

This is the reason why in accordance with the present invention it is particularly important to supplement plasma PL by the administration of vitamin B6 at least in part in the form of PL or an appropriate precursor of PL which does not depend on the intervention of oxidase or oxygen.

It is also preferred to employ such PL or precursor in a nonphosphorylated form in order to bypass dephosphorylation reactions induced by phosphatase enzymes.

Nevertheless, in order to stimulate the development of the oxidase enzyme system in the infant it is preferred to include modest amounts of PN or PN precursor in the preparation in addition to PL.

The ratio of PN:PL may be in the range 10:1 to 1:10, preferably 4:1 to 1:6 more preferably 2:1 to 1:3 e.g. 1:2.

Because the oxidase enzyme system is very sensitive to riboflavin deficiencies it is advisable to incorporate in the preparation riboflavin, e.g. in an mount of from 0,5 to 5 times, e.g. twice the amount of PN.

The daily dosages of the aforesaid ingredients per infant are:

| Component | Range mg | Preferred mg | More Preferred mg | Example mg |
|---|---|---|---|---|
| PL | 0.01–5 | 0.05–1.5 | 0.08–0.5 | 0.20 |
| PN | 0.01–5 | 0.03–0.5 | 0.05–1.5 | 0.1 |
| Riboflavin | 0.01–5 | 0.05–3.0 | 0.1–2 | 0.2 |
| Folate | 0.001–0.5 | 0.01–0.2 | 0.02–0.1 | 0.04 |
| Vit B12 | 0.01–10 mcg | 0.05–5 mcg | 0.1–2 mcg | 0.55 mcg |

Homocysteine, besides the various toxic effects already mentioned, also stimulates free radical induced oxidation, including that of cholesterol. This adds to the vascular damage directly induced by homocysteine, because once that first damage has been done, the blood vessels so damaged are in a condition in which they are vulnerable to the atherosclerotic action of cholesterol, and that action is performed by cholesterol mostly in its oxidised form.

This adverse effect is aggravated in infants by other factors, particularly in the case of bottle-fed babies. It has now been found that the thermal processes to which substitutes for human milk are subjected for bottle feeding purposes—boiling, spray drying—likewise result in the formation of dangerous oxy-cholesterol from the originally unoxidised lipids present in natural fresh milk.

In addition, applicant has surprisingly found that cow's milk besides containing four times more methionine than human milk, contains 6 times less selenium, 2–3 times less vitamin E, 4–6 times less vitamin C, 3 times less vitamin A and 2–3 times less nicotinic acid. In the context of the present invention it is pointed Out that vitamin C and E are important anti-oxidants by virtue of their ability to react directly with free radicals. The selenium on the other hand forms an integral part of the enzyme glutathione peroxidase, an enzyme which catalyses the chemical decomposition of biologically generated peroxides. Together, vitamins C and E and glutathione peroxidase form part of the body's important protective mechanism against free radical damage. The anti-oxidants in particular vitamin C also have the ability to counteract the effects of some of the products of free radical and oxygen activity already present in infant food formulations such as the aforesaid oxidised lipids.

Such anti-oxidants also reduce the risk of free radical damage resulting from excessive homocysteine accumulations in infants.

Accordingly, the present invention further proposes the preferred incorporation in the preparations according to the invention of an anti-oxidant preferably one or more of the substances d) vitamin C, e) vitamin E (e.g. as tocopherol acetate) and f) selenium (e.g. as selenium yeast), more particularly in amounts to provide the following daily dosages per infant:

d) 10–100 mg, preferably 20–80 mg, more preferably 40–70 mg, e.g. 50 mg e) 0.1–20 mg, preferably 0.5–15 mg, more preferably 1–10 mg, e.g. 4 mg f) 1–80 µg, preferably 3–20 µg, more preferably 5–15 µg.

From the aforegoing the range of suitable ratios in relation e.g. to vitamin B6 may be calculated.

Alternative or additional anti-oxidants for purposes of the present invention include carotenes (preferably B-carotene), ubiquinone and vitamin A.

Marginal zinc deficiencies are widespread in infants, particularly when bottle-fed. Applicant has surprisingly found that this is mainly due to poor absorption of zinc from cow's milk and proprietary infant foods. This problem can, according to the invention, be overcome by the inclusion of zinc in the preparation in the presence of substrates that will enhance and facilitate zinc absorption in the infant. According to the invention vitamin C and/or citrate are suitable for that purpose, and the incorporation of zinc citrate plus vitamin C is therefore a preferred integer of the invention. Zinc (in the form of zinc titrate) is advantageously employed in daily dosages (calculated as Zn) in the range of 0,1-20 mg, preferably 0,5-10, more preferably 1-8 mg, e.g. 4 mg Zn.

Human milk, but not cow's milk, contains substantial quantities of gamma linolenic acid (GLA), an important precursor of the prostaglandin 1-series in humans. Applicant has found that in some infants, especially premature infants, the enzymes required for producing GLA from its natural precursors are underdeveloped, resulting in further potential complications in addition to those outlined above. Accordingly the invention proposes in addition the incorporation in the preparation of GLA, to provide a daily dosage of 2-20 mg, preferably 6-10 mg.

Finally, because of the frequency of food allergies arising in bottle-fed infants, the invention proposes the incorporation in the preparation of an allergy suppressing substance. It has been found that extracts of finely ground plant material from the herb tea plant *Aspalatus contaminatus druce* or related species suitable for that purpose and is not only compatible with the above described ingredients of the preparation, but that its effect is in fact enhanced by these. This ingredient is employed in daily dosages of 1-20 mg, preferably 8-12 mg. The general pharmacological and toxicological properties of the individual ingredients of the preparations in accordance with the invention are well documented in the art and require no further description. The dosage rates in accordance with the invention are below accepted toxicity levels.

The effectiveness of the claimed combination for reducing elevated homocysteine has been tested in adults as described in the abovementioned co-pending application. The results of those tests can be extrapolated to infants. It was shown that the effect of the combination taught by the present invention is greater than the mere additive effect of individual ingredients.

DETAILED EXPLANATION OF INVENTION AND DESCRIPTION OF PREFERRED EMBODIMENTS

The following explanations and examples are to be read in conjunction with the more general description further above and with the claims to obtain a full disclosure of the present invention.

The invention teaches a new use in therapy and prophylaxis of pyridoxal or certain precursors thereof.

A preferred compound to be used in accordance with the invention is pyridoxal itself, because that is the compound which can be utilized directly to meet the deficiency. It is the only form capable of entering directly into tissue and other B6-deprived cells, in order to be converted there directly into pyridoxal phosphate (PLP) (the only active form of B6) by the action of kinase (and its co-factor adenosine triphosphate—ATP).

PLP can be administered, according to some embodiments of the invention, but is less preferred, because in the gut it must first be hydrolysed to PL before absorption can occur, and also in the plasma it must first undergo hydrolysis to PL before it can enter into the cells. Although the enzymes required for such hydrolysis are usually available in the gut and in plasma, the hydrolysis is not instantaneous and delays the availability of the PL in its non-phosphorylated form. Moreover, these enzymes can be inhibited by drugs in certain pathological conditions. On the other hand and because of these considerations, PLP can sometimes be utilised as an effective slow release form of PL, e.g. in dietary or pharmaceutical compositions for oral use in Cases, where these pathological conditions do not arise.

Pyridoxamine (PM) and its phosphate (PIMP) can also be used in addition to PL in dosages similar to those for PN. Pyridoxamine (i.e. the non-phoshorylated compound) can also enter the cell directly, in contrast to PMP, which like PLP must first be hydrolysed and in that respect suffers from the same disadvantages. Although PM requires oxidation to PL, as does PN, it was found to offer certain advantages over PN.

The enzymes which are needed to convert PM into PL are normally readily available, both inside and outside of the cells, so that the reason why PL is more preferred is mainly the potential delay caused by this reaction. A possible advantage of PM is its greater stability. However, the stability of PL in pharmaceutical formulations can be enhanced satisfactorily by antioxidants such as ascorbic acid (vit C) and/or sodium metabisulphite.

Pyridoxal can be employed in the form of pharmaceutically acceptable acid addition salts (e.g. the hydrochlorides) or of complexes capable of the rapid release of PL in vivo.

The following, in accordance with the invention, are examples of complexes and derivatives of pyridoxal capable of releasing pyridoxal readily in vivo, and are therefore ordinarily suitable for use instead of pyridoxal itself and in preferance to pyridoxine:

I) Addition salts of PL and pharmaceutically acceptable acids, for example: HCl (preferred), $H_2SO_4$, $H_3PO_4$, certain amino acids, e.g. glutamine, asparagine, glutamic acid;

II) Acetals, resulting from the addition of an alcohol to the aldehyde group of PL. A typical example is pyridoxal monoethyl acetal hydrochloride.

III) Condensation products arising from the reaction of the aldehyde group with
an amine, leading to the formation of amino alcohols or Schiff bases:

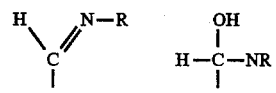

Schiff base      amino alcohol

The amine is preferably a biogenic or biological amine having desirable biological properties, e.g.

(1) Amino acids (e.g. L-lysine, L-arginine, glycine)

(2) Pyridoxamine (PM); both PL and PLP will react with PM or PMP to form a Schiff base derivative,

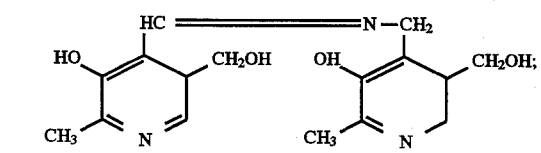

this Schiff base is a preferred derivative for the purposes of the present invention. In vivo it is a source of both PL and PM.

(3) Taurine (4) Suitable dimes, e.g. ethylenedime; ethylenedime reacts with PL to form a compound which in turn forms a sparingly soluble magnesium complex which may be used according to the invention as a source of both PL and Mg.

The invention is based on the realisation that in the aforesaid conditions, associated with often severely reduced blood and cellular B6 depletion, the administration of PL is substantially more effective than PN to counteract such depletion, being effective even in patients who do not respond to conventional administration of PN. A direct inverse correlation exists between the degree of B6 depletion of critically ill patients and their chances of survival. Medical and surgical complications such as shock, hepatic failure, infection and sepsis, wound dehiscence, incisional hernia, aminoglycoside induced renal failure and impaired skin and mucosal regeneration, hemato-poiesis, hormone production and wound repair; multi-organ dysfunction, respiratory distress and also severe depression are substantially more frequent in B6 deficient patients. These conditions are, inter alia, causally related to impairment of immune function, collagen and elastin cross-linking and polyamine synthesis and accumulation. Those patients who ended up with a plasma content of phosphorylated PL (i.e. PLP) of 20 nM or greater usually survived, and those with a final PLP content of 10 nM or less usually did not. Patients who were destined to die had a poor response to conventional B6 supplementation: their increment in plasma PLP with hyperalimentation and additional PN was generally less than 10 nM and occasionally less than 1 nM, even with 200 mg/day of PN. With hindsight the probable reasons why the administration of PL can surprisingly overcome or mitigate this problem will be explained further below in this specification. However, the correctness or otherwise of any explanations given or mechanisms postulated is not to limit the scope of the invention or to be relevant to the inventive merits of the invention as claimed.

As briefly shown in the general description of the invention, the inventive use of pyridoxal or its precursors for the management of depressed or inadequate intracellular PLP levels and increased vitamin B6 demand is broadly concerned with conditions wherein the PN-PLP pathway is disturbed or insufficient. This may be due to an intracellular oxidase and/or oxygen deficiency. It often also involves a kinase deficiency.

These situations of enzymatic disturbance or insufficiency may broadly be divided into two broad categories. The first category comprises those where the .disturbance or insufficiency is due to chemical factors (internal or externally introduced) which compromise the relevant enzymes and/or inactivate or remove intracellular PLP. The second category has as its common cause an inherent intracellular enzyme deficiency or defect. Some situations belong to both categories. Specific examples of these categories will be dealt with below.

The administration of PN is often ineffective to counteract the B6 depletion in these situations. The present invention teaches to administer PL instead, preferably intravenously, to provide a rapid supply of active B6 in plasma and cells.

It is believed that some of the superiority of PL over other B6 vitamins, in particular PN, is based on the combination of principles and mechanisms postulated in what follows, which appears to fit biochemical and clinical observations:

PLP, i.e. the phosphorylated form of PL, is the active form of B6 inside cells as well as in the blood plasma. However, none of the phosphorylated B6 vitamins (PLP, PMP, PNP) is able to cross biological membranes (except those of the healthy liver), so that the intracellular levels of essential PLP depend upon the intracellular availability of PL or PN, which are the main precursors of PLP and which readily cross cell membranes.

PN as used in conventional B6 preparations must pass through a series of enzymatic reactions before it becomes available inside the various cells in its active form, PLP. Although PN, being non-phosphorylated, is capable of crossing biological membranes and entering into cells, it is useless inside the cell unless firstly it is convened (either before or after entering the cell) by the kinase enzyme into PNP, and secondly (and this .must happen inside the respective cell) into PLP, by the action of the kinase enzyme.

PL kinase is widely distributed in the body, including the myocardium. In contrast, the PN(PNP) oxidase system is confined to a few tissues and is either absent or present in very low concentrations in the heart and most other cells. It is present in relative abundance only in the liver, and even there only if the liver function is intact. This leads to the important conclusion that in tissues other than the healthy liver there is a long lag period for the synthesis of PLP after parenteral injection of PN, since conversion of PN into PLP takes place essentially only in the liver. If the liver function is impaired or absent (depressed liver function or liver perfusion), as may often happen in severely ill patients, particularly when multiple organ disfunction has set in, the conversion of PN into PL and PLP is compromised and PN-supplementation is rendered ineffective. It is a unique property of healthy liver tissue (as contrasted with other cells) that it is able to release to the plasma PLP bound to albumin.

Moreover, the plasma half-life of PN in man is only about 12 minutes. The administration of high doses of PN under these conditions is in fact counterproductive. The initial step of PN activation inside cells may either be kinase induced phosphorylation to PNP (followed by oxidase catalysed oxidation to PLP) or initially oxidase induced oxidation of PN to PL (followed by kinase catalysed phosphorlation to PLP). Both PN and PL therefore compete for the same kinase enzyme, and in the presence of excess PN, the phosphorylation of PL is compromised. In addition it would appear that PN may inhibit the entry of PL into cells. PNP, once formed in any cells other than liver tissue, is metabolically trapped and is no longer available for conversion into PLP.

Administration of PLP is also less rapidly effective than PL. PLP must first be de-phosphorylated in the plasma (by the newly discovered PLP-specific phosphatases referred to above) before it can enter the cells where B6 is needed. This involves a delay and presupposes the availability of the necessary enzymes (phosphotase) and the absence of factors inhibiting these enzymes. Moreover, PLP is substantially more prone to becoming protein (albumin) bound than PL.

This confirms the inventive concept that administration of PL is the universally effective emergency procedure for restoring cellular B6 activity in serious disease conditions, whether or not this is accompanied by concomitant therapy with drugs that may be B6 antagonistic.

The clinical significance of PL was not previously recognised, inter alia because it was not appreciated that biological utilisation and activation of PN may be severely compromised in many acute disease condition, or that administration of PN under these circumstances may in fact be counterproductive in that high levels of PN not only suppress cellular PL uptake, but high intracellular PN levels compete with available PL for the common kinase enzyme system used to phosphorylate both PN and PL intracellularly. The PLP plasma levels cannot be restored to normal in some critically ill patients even by giving large doses of PN,

| Vitamer | Route | Daily adult dose (mg) | | | Daily dose mg/kg bodyweight | | |
|---|---|---|---|---|---|---|---|
| | | Range | Preferred | Optim. | Range | Preferred | Optim. |
| PL | i.v. | 2–300 | 5–150 | 10–100 | 0.03–4.28 | 0.07–2.14 | 14–1.43 |
| PM | i.v. | 2–300 | 5–150 | 10–100 | 0.03–4.28 | 0.07–2.14 | 0.14–1.43 |
| PM | i.v. | 2–350 | 5–250 | 10–150 | 0.03–5.0 | 0.07–3.57 | 0.14–14 |
| PLP | i.v. | 2–350 | 5–250 | 10–150 | 0.03–5.0 | 0.07–3.57 | 0.14–2.14 |
| PL | i/m | 3–400 | 5–200 | 10–150 | 0.042–5.7 | 0.07–2.89 | 0.14–2.14 |
| PM | i/m | 3–400 | 5–200 | 10–150 | 0.042–5.7 | 0.07–2.89 | 0.14–2.14 |
| PLP | i/m | 5–450 | 10–300 | 20–200 | 0.07–6.42 | 0.07–4.29 | 0.28–2.86 |
| PMP | i/m | 5–450 | 10–300 | 20–200 | 0.07–6.42 | 0.07–4.29 | 0.28–2.86 |
| PL | s/c | 3–500 | 5–250 | 10–200 | 0.042–7.14 | 0.07–3.57 | 0.14–2.16 |
| PM | s/c | 3–500 | 5–250 | 10–200 | 0.042–7.14 | 0.07–3.57 | 0.14–2.86 |
| PLP | s/c | 7–500 | 10–300 | 10–250 | 0.10–7.14 | 0.14–4.280 | 0.14–3.57 |
| PMP | s/c | 7–500 | 10–300 | 10–250 | 0.10–7.14 | 0.14–4.28 | 0.14–3.57 |
| For oral administration | | | | | | | |
| PL | | 2–500 | 5–250 | 10–200 | 0.03–7.2 | 0.07–3.6 | 0.14–2.9 |
| PM | | 2–500 | 5–250 | 10–200 | 0.03–7.2 | 0.07–3.6 | 0.14–2.9 |
| PLP | | 2–500 | 5–250 | 10–200 | 0.03–7.2 | 0.07–3.6 | 0.14–2.9 |
| PMP | | 2–500 | 5–250 | 10–200 | 0.03–7.2 | 0.07–3.6 | 0.14–2.9 | since those patients are no longer in a position to benefit metabolically from such treatment.

One crucially important, not previously known reason for the superiority of pyridoxal and the said precursors as a vitamin B6 supplement in the treatment or prophylaxis of depressed or inadequate intracellular pyridoxal phosphate levels arises from the unexpected discovery that a substantial percentage of patients suffer from an inherent intracellular impaired ability to convert pyridoxine into pyridoxal phosphate. Such impaired ability can be associated with some of the pathological conditions described further above. However, quite surprisingly about 20% of humans suffer from such relative inability genetically. This then takes us to the second major category of disturbed or insufficient PN-PLP pathways, i.e. inherent intracellular enzyme deficiency or defect.

The present invention provides a pharmaceutical or dietary composition and method of treatment for the supplementation of vitamin B6 deficiency in plasma and cells—tissue cells as well as blood cells—caused by pyridoxine—non-responsive conditions (or conditions that respond poorly to PN) due to newly discovered instances of enzyme (especially PN-oxidase) deficiency or polymorphism in organs and cells which are normally available for pyridoxine utilisation. Such deficiencies are of special clinical relevance under the following conditions:

A) cellular immaturity, for example in premature infants; excessive need for replacement of damaged or destroyed cells, which replacement may occur:
  (i) from less specialised precursor cells
  (ii) by normal cell division
B) genetic enzyme insufficiency, in particular oxidase deficiency or polymorphic aberration
C) Enzyme (e.g. oxidase and PLP-specific phosphatases) inhibition due to
  (i) disease-produced toxins, including polyamines
  (ii) drugs;

As regards dosage forms and dosages, and potentiators, essentially the same principles apply as in the earlier discussed cases.

Dosage Rates for Parenteral Administration to Children (Not Infants) and Adults

The dosage forms preferably include a suitable source of zinc, e.g. zinc chloride, zinc sulphate (or other physiologically acceptable zinc salt) or zinc oxide, preferably in an mount suitable to provide a dosage of zinc of:

10–20 mg per day as Zn (for adult)=0.15–0.30 mg/kg/day

Range: 0.05–0.9 mg/kg/day

Preferred: 0.1–0.5 mg/kg/day

Optimal: 0.15–0.3 mg/kg/day

The dosage forms preferably include a suitable source of magnesium, e.g. pharmacologically acceptable salts of magnesium such as magnesium chloride or magnesium aspartate, or magnesium oxide, or magnesium titrate; preferably in an amount suitable to provide a dosage of magnesium of:

100–300 mg per day as Mg (adult)=1.5–4.3 mg/kg/day

Range: 0.5–10 mg/kg/day

Preferred: 1.0–5.0 mg/kg/day

Optimal: 1.5–4.3 mg/kg/day

The different newly discovered situations involving inherent intracellular reduced capability or inability to utilise PN metabolically will be discussed more fully in what follows.

Cellular Immaturity

Premature infants: From a detailed comparison of the wide diversity of known facts with own findings it has now been concluded that full term infants are usually already able to convert dietary or pharmaceutically administered PN adequately to satisfy the substantial Vitamin B6 requirements of the growing body and its metabolism, but premature infants are not or not sufficiently so able, particularly not before a stage in gestational age which in most infants is between about 28 to 30 weeks. The lower the gestational age the more severe is this deficiency. The present inventor has been able to identify, as the primary cause of this deficiency, the inability of the immature system of the infant to produce the enzyme oxidase. The deficiency is aggravated by the defective tissue-oxygenation which is often present in premature infants.

To overcome this deficiency in premature infants using conventional pyridoxine supplementation would require several tens of times more than the expected dosage rate. However, such high dosages of pyridoxine are highly undesirable, particularly when administered in bolus form. Such high dosages will then exceed the capacity of the liver, and this in turn will result in excess pyridoxine in the plasma, from where it enters the various body cells (tissue and RBC) through the cellular membranes in competition with the limited supply of PL. Once inside the cell this PN now competes against intracellular PL for whatever kinase is available in the cell to form PNP instead of the required intracellular PLP. The PNP, which is useless in the absence of adequate oxidase activity, is trapped inside the cell there to compete further with PLP for vital enzyme sites. The above described phenomena resulting from excessive dosages of pyridoxine may result in toxic effects and (paradoxically) in symptoms similar to those of vitamin B6 deficiency.

Premature infants may be treated parenterally in the acute stages followed by oral administration of PL either in the form of paediatric drops or as an ingredient of an appropriately constitute infant food formula.

Suitable dosage rates are as follows:

For Parenteral Administration to Premature Infants

| Vitamer | Route | Range Dose (mg) (daily) | Range Dose (mg/kg) bodyweight (daily) | Preferred Range Dose (mg) (daily) | Preferred Range Dose (mg/kg) bodyweight (daily) |
|---|---|---|---|---|---|
| PL | i.v. | 0.003–3.0 | 0.01–1.0 | 0.01–0.4 | 0.03–0.13 |
| PLP | i.v. | 0.006–6.0 | 0.026–1.0 | 0.02–0.5 | 0.06–0.16 |
| PL | i/m | 0.005–6.0 | 0.017–2.0 | 0.02–0.5 | 0.06–0.16 |
| PLP | i/m | 0.006–9.0 | 0.02–3.0 | 0.03–0.6 | 0.1–0.2 |
| PL | s/c | 0.005–6.0 | 0.017–2.0 | 0.02–0.5 | 0.06–0.16 |
| PLP | s/c | 0.006–9.0 | 0.06–3.0 | 0.03–0.6 | 0.1–0.6 |

The active B6 vitamins may be supplied in lyophilised form in dark coloured ampoules sealed under nitrogen in convenient quantities. The contents may be dissolved in saline and added to the contents of any suitable infusion solution at a rate indicated above.

For Oral Administration to Premature Infants (i) Paediatric drops

These are formulated in an appropriately constituted flavored base with added vitamins and minerals as in the accompanying example in such a manner that the following preferred dosage rates are achieved:

| Vitamer | Range Dose (mg) (daily) | Range Dose (mg/kg) bodyweight (daily) | Preferred Range Dose (mg) (daily) | Preferred Range Dose (mg/kg) bodyweight (daily) |
|---|---|---|---|---|
| PL | 0.03–3.0 | 0.01–1.0 | 0.1–0.5 | 0.003–0.16 |
| PLP | 0.05–5.0 | 0.016–1.6 | 0.15–0.6 | 0.05–0.2 |

The preferred vitamin is PL.

(ii) PL-fortified infant food

An infant food is formulated complying with all the usual requirements applicable to infant food formulae with regard to protein, energy, vitamin and mineral contents. B6 vitamins are included in such a manner that the daily intake is essentially as in the previous table.

The preferred vitamin is PL itself

Alternatively tablets may be formulated for use with proprietary infant food formulae in such a manner that essentially the same amounts as listed above are administered. Such tablets are manufactured by processes known in the art in such a way that they will dissolve and disintegrate rapidly in aqueous media such as infant food formula dilute glucose solution or in fruit juices and the quantities per tablet may be such that the full dose is contained in one tablet (to be used only once daily) or the daily dose may be subdivided over 2 to 6 tablets to be used with two feeds (e.g. morning and evening) or more often, e.g. with every feed.

In one preferred embodiment pyridoxal (or any one of the other vitamins listed) may be used in conjunction with a small quantity of pyridoxine (and riboflavine) in the form of both pediatric drops or tablets in order to stimulate liver enzyme development in the infants in such a manner that the following preferred dosage rates are achieved.

| Vitamer | Range Dose mg (daily) | Range Dose mg/kg bodyweight (daily) | Preferred range Dose mg (daily) | Preferred range Dose mg/kg bodyweight (daily) |
|---|---|---|---|---|
| PL | 0.024–2.4 | 0.008–0.8 | 0.16–0.4 | 0.053–0.13 |
| PM*) | 0.024–2.4 | 0.008–0.8 | 0.16–0.4 | 0.053–0.13 |
| PLP | 0.04–4.0 | 0.013–1.3 | 0.24–0.5 | 0.08–0.17 |
| PMP*) | 0.04–4.0 | 0.013–1.3 | 0.24–0.5 | 0.08–0.17 |
| PN | 0.02–3 | 0.007–1.0 | 0.1–1.0 | 0.03–0.3 |
| Riboflavin | 0.02–3 | 0.007–1.0 | 0.1–0.6 | 0.03–0.2 |

*)as an alternative or partial alternative to PN

Replacement of Damaged or Destroyed Cells

In the human or animal host, the response to disease-induced or trauma-induced cellular damage is invariably growth stimulation to replace functionally incapacitated cells. Growth processes may include division of cells to produce daughter cells or it may involve cellular replacement through activation of a chain process by means of which non-differentiated precursor cells divide and ultimately develop through various stages to replace the damaged cells such as may occur after the destruction of red blood cells in disease.

In many cases, including normal healing, the regenerating cells go through a phase of rapid replication or, as in the case of red blood cell regeneration, precursor stem cells in the bone marrow proliferate to produce a series of intermediate cells culminating in an increased red cell population. The fundamental concept upon which this aspect of the present invention is based is that such rapidly regenerating cells have vitamin B6 growth requirements that differ from those of normal cells. This concept applies to individual cells, and to individual organs (e.g. the liver), and is thus analogous to the case of the premature growing infant or fetus.

In all cells, the basic requirements for growth are energy, proteins (amino acids), lipids, carbohydrates and a variety of co-factors (vitamins, minerals) which are necessary for optimal enzyme action. Amongst these, vitamin B6 activity is of special significance and is frequently a limiting factor due to the fact that B6 plays such a pivotal role in protein metabolism and energy production.

A particular application of this aspect of the invention relates to the replacement of highly differentiated cells from less differentiated precursor cells. Red blood cells (RBC) are important examples, as are other cellular elements of the blood. In all such cases the intermediate or more primitive precursor cells are better able and equipped to utilise PL rather than PN as a source of vitamin B6 activity.

A common undifferentiated primitive stem cell in the bone marrow gives rise to lymphocytes, red blood cells, granulocytes, monocytes, platelets and others in the course of which it is transformed into a variety of precursor cells. In the case of the RBC formation, this process involves the following:

Undifferentiated stem cell - - - Proerythro blast - - - Basophilic erythroblast

Polychromatic erythroblast - - - Acidophylic erythroblast - - - Reticulocyte - - - Erythrocyte (RBC)

Similar cascades exist in the case of the other cellular elements in the blood including platelets. A fundamental observation was the fact that a bone-marrow aspirate containing the more primitive, undifferentiated cells was found to be incapable of converting PN into PLP or PL, thus demonstrating for the first time the absence of PNP-oxidase activity in such immature cells. This has extremely important practical significance, since the developing RBC require PLP for haeme and haemoglobin synthesis.

The normal mature RBC is perfectly capable of utilising PN as a source of B6 activity, wherefore in health, when no special demands exist for RBC formation, PN is an adequate source of B6 activity in RBC. However, in any disease process during which an increased demand for RBC production may exist, the rate of RBC production may be compromised if inadequate B6 activity inside the cells exist, and during such an emergency the required B6 activity cannot be supplied by supplementation with PN, since the stem cells from which RBC are formed are incapable or at best have a reduced capability of utilizing PN for this purpose. The developing RBC require optimal B6 activity inside the cells for various reasons including the critical B6 requirement for haemoglobin synthesis and for energy production. In the RBC, 90% of energy is derived from the process of glycolysis, several steps of which are B6 dependent, including glucose production from glycogen (B6 dependent glycogen phosphorylase) and several transamination reactions. The process is also critically dependent on the free availability of adequate quantities of magnesium.

Having regard to the aforegoing, the invention according to a particularly important aspect thereof provides a pharmaceutical composition for the treatment of conditions involving a destruction or shortage of red blood cells and/or of haemoglobin, comprising a content of pyridoxal in a dosage form and concentration designed to deliver dally to a patient from 0,01 to 7,0 mg pyridoxal per kg body mass, the pyridoxal being optionally present in the form of a complex or soluble addition salt which in vivo readily releases pyridoxal.

The invention provides the means for a new treatment of such conditions involving a new therapeutic mechanism. It is applicable to a wide range of diseases involving a shortage of haemoglobulin-synthesising red blood cells and/or of haemoglobin.

A deficiency of haemoglobin in the blood is called anaemia, of which many types are known. They all cause pallor, fatigue and breathlessness. In severe cases the nervous system may be damaged permanently, and death may result. The direct conventional treatment of one form of anaemia usually involves the administration of iron to supplement an iron deficiency, iron being needed by normal mature erythrocytes for the synthesis of haemogoblin. However, this presupposes the availability of an adequate supply of erythrocytes capable of performing such synthesis. Many forms of disease result in a shortage of these cells.

Such diseases may involve failure of the bone marrow to produce sufficient red blood cells, causing aplastic anaemia. In the past this condition could only be relieved by transfusion, bone marrow transplantation or by marrow stimulating agents including vitamin B12.

Merrill and Henderson (Am. Rev. Nutr., 1987.7, 137056) on page 144 describe the treatment of "pyridoxine-responsive" anemias with pyridoxine. In spite of the relatively high dosages (50–200 mg PN/day) and in one case even 600 mg/day) the response rate was stated to be "optimal" in fewer than half of the cases. The explanation given is not in accordance with applicant's findings. Other forms of anemia are non-responsive. The reference does not support the new approach according to the present invention. The toxic side effects of high dosages of PN are confirmed by what is stated on page 147.

Haemolytic anaemia is caused by excessive haemolysis of red blood cells, causing anaemia and jaundice. Such haemolysis may have several causes, one being the various protozoal diseases in man or animals, wherein the protozoa proliferate in and destroy the red blood cells. These include in man malaria (four different plasmodium species), bartonellosis, and in animals Rift Valley fever, corridor disease, biliary fever (*Babesia canis*).

Red blood cells are also destroyed by other types of micro organisms, e.g. certain viruses, such as parvo virus B19.

Some of the diseases which destroy red blood cells also destroy other cells, the regeneration of which is favourably influenced by the administration of pyridoxal or its precursors according to the invention, e.g hepatocytes in the case of malaria.

A further benefit resulting from the invention in the present context is the fact that toxins and polyamines are frequently released during disease which additionally compromise the ability of the body to utilise pyridoxine. Also, some of the drugs used in combatting such diseases have that side effect. Pyridoxal plays an important role in overcoming the resultant B6 deficiency.

In many diseases, blood polyamine levels rise sharply due to disease-induced cellular death and disintegration. Polyamines are essential constituents inside living cells, where they are essential for macromolecular synthesis, but increased concentrations outside cells such as may occur during certain diseases are toxic due inter alia to the fact that they are known to react chemically with PLP, the resulting complexes being eliminated in the urine. We have now surprisingly found that polyamines and/or other disease-produced toxins may also inhibit the B6-activating enzyme system as well as the natural PLP-hydrolysing phosphatases and that this is one of the mechanisms by which increased toxin and polyamine levels produced in disease are toxic. This is of particular relevance to RBC haemeostasis since, in general, disease-produced polyamines are to a large extent transported inside RBC, and specifically in the case of malaria there is a marked parasite-related increase of polyamines inside RBC, whereas normally there are only trace amounts of polyamines inside RBC. RBC infected with malaria parasites therefore have a reduced capacity to utilize non-phosphorylated B6 vitamins such as PN a further advantage of supplementation with the appropriate B6 vitamin PL or PM. In addition, accumulated intraerythrocytic polyamines (in disease) will react and thus remove PL and PLP, thereby creating an increased demand for the production of these co-factors.

Anaemia may also be caused by abnormalities of the red blood cells, as happens in macrocytic anaemia or in sickle cell anaemia, and in many of these cases patients may benefit to a varying degree from the administration of PL.

Anaemia may result from nutritional causes or from severe blood loss, due to various causes, including menstrual abnormalities, and in such cases PL is superior to PN in restoring the B6 component of the deficiency.

It has now been discovered surprisingly that pyridoxal is capable of stimulating the formation of haemoglobulin even in many cases where conventional forms of therapy are ineffective or inadequate, and specifically in some cases of so-called "pyridoxine refractory" or "pyridoxine non-responsive" anaemias.

It follows from the aforegoing that the composition and method are specifically recommended for the treatment of the aforedescribed conditions, i.e. anaemia, malaria, babesia canis infections and others with similar metabolic features.

It follows further that the invention can be applied to improving blood transfusion preparations and blood substitutes by the incorporation therein of an appropriate content of pyridoxal or one of the substances referred to which release PL in vivo or similarly by one of the other non-pyridoxine type of B6 vitamins.

In contrast to some other vitamins, the physiology and biochemistry relating to B6 differs relatively little between humans and animals. Accordingly, what has been described in the aforegoing in relation to humans is applicable also to veterinary medicine. Accordingly, the scope of the invention extends to veterinary medicine in relation to all aspects of the invention. The pharmaceutical compositions may be applied in the treatment of animal diseases and surgery substantially in a manner analogous to the treatment and prophylaxis described for humans.

The following table summarises a number of microbial diseases in man or animals involving large-scale cell destruction by intracellular or extracelllular infections:

In that table a number of microbal diseases are shown. All of these are responsible for cell death of the "affected cells". The dead cells release polyamines and in many cases toxins are also released—either by the dead cells or the microbes or both, whereby PLP is depressed and the PN-PLP pathway is compromised. Where the affected cells are blood cells, they have to be replaced in the bone marrow by the "cascade" procedure described further above. These cells play an important role in the PN-PLP pathway. Stimulated by the increased cell demand these newly formed blood cells enter the circulation in an immature state in which they cannot yet perform their PN-PLP pathway function. The replacement of the remaining cells takes place by in situ cell division, followed by cell growth of these daughter cells. This process requires the availability of adequate amounts of PLP which the young cells themselves cannot supply and which availability is compromised by cell death. The invention shortcuts the PN-PLP pathway by the direct supply of PL which can enter the cells readily for in situ conversion into intracellular PLP.

| AFFECTED CELLS | INTRACELLULAR VIRUS | INFECTIONS PARASITE RICKETTSIA | PARASITE FUNGI | EXTRACELLULAR INFECTIONS BACTERIA |
|---|---|---|---|---|
| Red blood cells | Parvovirus B19 | | Malaria | |
| T-lymphocytes | HTLV-I;CWV HIV; HHV-6 | | | |
| B-Lymphocytes | EBV;HHV-6 | | | |
| Macrophage | | Mycobacteria Salmonella Listeria | Histoplasma Blastomyces | |
| Vascular endothelium | | Rickettsiae | | |
| Gut epithelium | Enterovirus | | Cryptosporidium Isospora | Shigella Salmonella Camphylobacter |
| Enterocyte | Rotavirus Adenovirus | | | |
| Non-keritinized squamous epithelium | Papillomavirus Herpes simplex virus | | | |
| Keritinized epithelium | Papillomavirus | | Dermatophytes | |
| Respiratory tract epithelium | Influenzavirus Resp sinsitielevirus | Mycoplasma | | |
| Glial cells/Neurones | Enterovirus Polyoma JC | | Toxoplasma | |
| Hepatocytes | Hepatitis A virus Hepatitis B virus Hepatitis D virus Hepatitis NANB viruses Yellow fever virus | | Toxoplasma Malaria | |

HTLV-I = Human T-cell lymphotropic/leukemia virus I
HIV = Human Immmodeficiency virus
EBV = Epstein Barr virus
CMV = Cytomegalovirus-6
HW-6 = Human Herpesvirus-6

The above comments in the context of RBC, relating to toxins, polyamines and side effects of drugs used in the treatment apply also to many of these diseases.

In addition to the organisms in the above table, rickettsia are also to be considered in such diseases as epidemic typhus, Rocky Mountain spotted fever, Q-fever, heartwater (in cattle).

Genetic Enzyme Polymorphic Aberration

It has now been discovered quite unexpectedly that about 20% of a normal human population have a genetic aberration (polymorphism) in their enzyme system which impairs their ability to convert pyridoxine into pyridoxal. Of course, if that condition coincides with any of the situations giving rise to vitamin B6 deficiency even in otherwise "normal" persons, such persons are especially compromised when put on conventional pyridoxine supplementation. These are the so-called "poor responders" or "non-responders" to PN therapy.

The enzyme glutamate-pyruvate-transaminase (GPT) is a PLP dependent enzyme present in RBC which can be used to assess the utilization of PN by RBC. In the population, individuals may be divided into 3 different groups corresponding to 3 polymorphic forms of the enzyme (1–1, 25%; 1–2, 50%; 2–2, 25%.

Approximately 20% of all persons studied (belonging to all 3 groups) were found to be slow responders to oral PN, RBC GPT-activity having been measured at day 0 and day 28 before and after daily oral supplementation with PN (10 mg).

It has now been found that these slow reactors have a genetically determined PN-oxidase enzyme defect.

The presence of 20% "slow-reactors" in the population now explains for the first time why in a variety of so-called B6 responsive diseases (premenstrual tension, depression, anaemia) it has frequently been found that approximately 80% of patients respond well to the drug but that the response rate is seldom 100%.

We have now surprisingly found that such patients have reduced PN-oxidase activity and that they do respond much more satisfactorily to PL or PM administration than to PN.

The above novel observations have important clinical implications. Twenty per cent of all patients previously discussed (e.g. in infections affecting RBC B6 status or infection similarly affecting B6 status of other cells or otherwise compromised B6 status due to serious disease or drugs) will be more seriously at risk than the remaining 80%. A further aspect of the present invention provides for a suitable test to determine intracellular PN-oxidase activity and thus to identify such patients which may then receive early and pre-emptive treatment as discussed more fully below.

In applying the present invention it is furthermore proposed to combine this with appropriate quantitative or semi-quantitative diagnostic tests for PNP-oxidase activity in tissue homogenates and red blood cell haemolysates. Such tests may be used to identify patients suffering from the aforesaid genetically impaired oxidase activity, who are particularly at risk in any situation where vitamin B6 supplementation is needed and who then definitely require the administration of a source of B6 other than pyridoxine.

Such tests are described in the aforesaid allowed parent application and may also be employed to identify and quantify the extent of any oxidase deficiency to which this invention relates.

Identification of Subjects Genetically Deficient in the Enzyme Pyridoxamine Phosphate Oxide (PPO)

Using the above analytical system, the following cut-off point is adopted which allows for the identification of genetically deficient individuals.

| Type of patient | n mol PLP + PL/g Hb/h |
| --- | --- |
| Normal | above 4.30 |
| Genetically deficient | below 4.3 |

The following typical results were obtained in a healthy adult human population: Erythrocyte oxidase activity: Normal patients: 20–150 E/g Hb/h. Patients with deficient oxidase activity: below 20 E/g Hb/h.

EXAMPLE 1

Clinical Trials on Dogs with B. canis Infection

Babesia canis infection, better known as "biliary fever", is a severe and frequently fatal disease in dogs. It is a protozoal disease involving large-scale destruction of erythrocytes (red blood cells) and loss of haemoglobin. Double blind trials were carried out on two groups of dogs presented to the clinic for treatment of severe B. canis infections. Upon admission, all animals were recumbent with fever, jaundice, and accelerated heart and respiratory rate. All animals were given standard treatment, which consisted of post surgical drip, doxycycline, trypan blue, hepavet, electrolytes and glucose. In the experimental group, a solution of PL was added to the drip (electrolytes, glucose) given to the animals. In the control group, saline was given to replace the PL solution.

The PL solution according to the invention was made up as follows (per vial):

Pyridoxal hydrochloride 243 mg (=200 mg PL)

Ascorbic acid 10 mg

Experimental Treatment

Experimental animals: PL solution according to the invention was given with the drip in such a manner that each patient received 50 mg of pyridoxal over a 12 h period. Each animal received only one such course of treatment.

Control Animals

These received saline instead of PL solution under similar conditions. Control animals were selected to resemble experiental animals as closely as possible in respect of race and initial haemoglobin concentration. The results are given in the following table.

| | Hb* (g/l) | RCC (×10$^{12}$/l) | Ht (l/l) | MCV (fl) | MCHC (g/dlRC) | WCC (×10$^9$/l) |
| --- | --- | --- | --- | --- | --- | --- |
| E** | 11.0 | 0.41 | 2.1 | −6 | 3.8 | 3.0 |
| E | 12.8 | 0.49 | 4.2 | 2 | −1 | −8.4 |
| E | 6.5 | 0.47 | 3.6 | 0 | −2.5 | 2.5 |
| E | 9.5 | 0.41 | 4.2 | 3 | −1.7 | 3.1− |
| E | 7.8 | 0.23 | 2.3 | 1 | −0.5 | 1.05 |
| E | 24.8 | 0.64 | 5.4 | 1 | 2.5 | 17.9 |
| Total | 70 | 2.65 | 21.8 | 1 | −8.2 | 27.15 |
| Average*** | 11.7 | 0.44 | 3.63 | 0.17 | −0.03 | 4.52 |

-continued

| | Hb* (g/l) | RCC (×10¹²/l) | Ht (l/l) | MCV (fl) | MCHC (g/dlRC) | WCC (×10⁹/l) |
|---|---|---|---|---|---|---|
| C | 3 | 0.18 | 1.19 | 1.25 | −1.5 | −3.4 |
| C | 12 | 0.53 | 4.1 | −1.7 | 0 | −4.4 |
| C | 2 | −0.01 | 1.0 | 12 | 7 | 17.8 |
| C | −1 | −0.04 | 0.8 | 6.0 | −2.7 | −0.5 |
| C | 9 | 0.42 | 3.7 | −1.2 | −1.4 | 2.1 |
| C | 6.8 | 0.24 | 3.9 | 0.3 | 4.3 | −7 |
| Total | 31.8 | 1.31 | 12.9 | 18.3 | −2.9 | 4.6 |
| Average | 5.3 | 0.22 | 2.55 | 3.17 | −0.48 | 0.76 |

Hb*: Haemoglobin (g/l)
RCC: Red cell count (×10¹²/l)
Ht: Haematocrit (l/l)
MCV: Mean corpuscular volume (fl)
MCHC: Mean corpuscular haemoglobin content (g/dlRC)
WCC: White cell count (×10⁹/l)
**E: denotes experimental animals C: denotes controls, E: denotes changes per day during the period between the first two series of measurements of the parameters listed. Norman these represent measurements obtained immediately after admission (or 1 day later) and again 2 to 4 days later after treatment has been started
***Average changes for six animals in each group over the two periods of measurement.

Conclusions

Clinical: The clinical observation was that animals on the PL infusion responded 21.0 much better to treatment than controls. These animals were significantly improved after 2 to 3 days judged on the basis of movement, water and feed consumption and alertness. Normally, as in the case of the controls, the animals only reach this stage of clinical improvement, if at all, after 5 to 6 days.

Haematological: Large, significant differences are reflected in several important 5 parameters between experimental and control groups (haemoglobin, RCC, WCC). These are fully consistent with the clinical observations. Inter alia, there had been an amazing recovery of haemoglobin levels, substantially in excess of what could be explained in terms of normal rates of formation of new mature red blood cells, capable of synthesising haemoglobin in the normal manner.

This example illustrates the benefits of PL administration in diseases involving destruction of erythrocytes. It has far-reaching implications and applications far beyond biliary fever in dogs. The erythrocytes are formed in the bone marrow, where (in humans), they take about 120 days to mature into cells capable of synthesising haemoglobin. For this synthesis pyridoxal phosphate is needed; however, the availability of pyridoxal phosphate depends on the availability of adequate activity of certain enzymes, in particular oxidase. In the immature erythrocytes a shortage of oxidase prevails, resulting in a shortage of pyridoxal phosphate and a resultant compromised ability to synthesise haemoglobin. In many pathological conditions the enzymes responsible for the formation of pyridoxal phosphate are, moreover, inhibited. In addition, the biogenic polyamines released in some pathological conditions leading to anaemia (as in biliary fever), as well as medications conventionally employed in the treatment of these diseases, aggravate the shortage of pyridoxal needed for haemoglobin synthesis.

Further Clinical Trials on Dogs with B-canis Infection

The experiment was repeated with 13 dogs (10 inbred beagles and 3 other mongrels) randomly divided into an experimental and a control group. All animals were infected with Babesia canis by injection of blood from a splenectomised donor dog which led to the development of acute Babesiosis in approximately 3–5 days. All dogs were monitored twice daily until the haematocrit values fell to 0.15 l/l when treatment was started which in the case of all animals consisted of the following:

Electrolytes solution (number 2) for the first 24th, thereafter Post-Surgisol. Both fluids were administered by means of an intravenous jugular catheter at a rate of 80 ml/kg/24 h.

Trypan blue (1%) 1 ml/kg intravenous once only. Berenil 3.5 mg/kg intramuscularly 7 days after the Trypan blue. Heparin, 25 IU/kg subcutaneously three times per day for the first 2 days.

Experimental animals, in addition, received pyridoxal in their infusions at a concentration of 50 mg/l for the entire duration of fluid therapy.

Before the start of treatment, a urine dipstick and sediment examination were performed as well as a complete clinical evaluation and faecal flotation to determine the presence of helminth ova.

Assessment: Temperature pulse and respiration were measured every 6 hours during the first 3 days and a subjective assessment of habitus (grade 1–4) and appetite (1–4) was also made at the same time.

Full haematological and biochemical assessment was performed daily.

Serum alkaline phosphatase determinations were made on days 1 and 3.

Additional trial parameters and measurements consisted of Astrup determinations (before treatment and again 24 hours later) and a ten day survival rate.

Samples for haematology were drawn in evacuated EDTA tubes and for serum chemistries into plain evacuated tubes (cephalic vein).

Plasma PLP and PL as well as RBC-PLP and PL values were determined by means of a HPLC procedure routinely used for human studies.

The following results were obtained

Two animals died in the control group and none in the experimental group. There was a definite clinical improvement in the experimental group consistent with the observations in the first experiment.

During the first 3 days (the decisive period which determines survival or not) there were significant differences in normablast count profiles: a continuous downward trend in the control animals and an inverse trend in the experimental group. Reticulocyte counts responded quicker in the experimental.

Whereas alkaline phosphatase values decreased in the control group from day 1 to day 3, there was a large increase in this parameter in the experimental group. Differences between the 2 groups were large and a definite trend discernable.

The mean corpuscular volume and the mean corpuscular hemoglobin were statistically significantly increased in the experimental animals at day 5.

EXAMPLE 2

Pyridoxal Infusion

Dissolve in sterile distilled water and dilute to 100 ml:

| | |
|---|---|
| pyridoxal hydrochloride | 4860 mg (= 4000 mg pyridoxal) |
| ascorbic acid | 1000 mg |
| sodium dihydrogen phosphate | 40 g |

Adjust pH to 6.5

Distribute 5 ml portions in amber coloured ampoules and lyophilise. Heat sterilise (10 min).

Administer as an infusion by dissolving in sterile saline and admixing the appropriate quantity with any other standard infusion or drip that the patient may be receiving (electrolytes, glucose) so that the dosage rates for parenteral administration as detailed herein will be achieved.

Alternatively, dissolve in 5–10 ml sterile saline and administer by intramuscular injection to achieve the dosage rate as specified herein.

EXAMPLE 3

Examples of Stabilised Solutions of PL a) To 100 mg of PL in 20 ml pH 7.0 Sorensen buffer (0.05 M) are added:

| | |
|---|---|
| Sodium metabisulphite: | 30–72 mg |
| Glucose: | 68–136 mg |
| Vitamin C: | 20 mg |

Filter seal in brown ampoules.

Heat sterilise at 50° C., 10 days.

Make up to 100 ml with sterile, distilled water and finally sterilise by filtration. Store in brown ampoules under nitrogen. To be used as in previous example.

EXAMPLE 4

Pyridoxal-supplemented Blood Substitute or Plasma

Pyridoxal hydrochloride (e.g. in sterile, amber coloured ampoules containing 200 mg of pyridoxal) is dissolved in 5 ml sterile saline solution and transferred to any commercially available blood substitute or transfusion solution in such a manner that, during infusion, the quantity of pyridoxal administered to the patients will be essentially as hereinbefore specified.

EXAMPLE 5

Pyridoxal-fortified Additive for Use with Conventional Plasma Expanders and Blood Transfusion Dissolve in 100 ml of sterile water and adjust pH to 6.5:

| | |
|---|---|
| Pyridoxal.HCl | 4860 mg |
| Ascoibic acid | 1000 mg |
| Sodium dihydrogen phosphate | 40 g |

Distribute in 5 ml amber coloured ampoules and lyophilise.

Dissolve contents of ampoule in 5 ml sterile saline and add to infusion solution (blood, plasma, plasma expander) on the following basis:

1 ampoule per 2–5 l.

EXAMPLE 6

Use of Pyridoxal in the Treatment of Malaria

Two groups of malaria patients are treated with pyridoxal. All patients receive standard treatment considered appropriate by the clinician in attendance consisting of anti-parasitic medication with supporting therapy to combat anaemia and possible lactate acidosis.

Clinical protocol

Group 1: These are seriously ill patients with malaria according to the WHO criteria for severe complicated malaria. Haemoglobin values are below 10 g/dl in these patients with cerebral malaria who are treated in an ICU. Generally the patients present with renal failure (creatinine 250 u mol), respiratory failure, severe electrolyte and acid-base imbalance, severe parasitaemia (more than 5% infected cells), billrubin more than 50 μmol/l; hypotension with bleeding abnormalities.

The patients receive normal standard treatment. In addition, the patients are given pyridoxal (200 mg per ampoule) by dissolving the contents of one ampoule in 5 ml sterile saline and adding the resulting solution to a standard electrolyte infusion solution. The rate of administration is such that the patients receive 100 mg pyridoxal/24 h for the first 3 days and thereafter 50 mg/day for another 2 days.

Group 2: These are less severely ill patients or patients recovering from severe malaria. They are treated conventionally, in addition with pyridoxal (or less preferably pyridoxamine) by oral administration at a dosage rate as described above, in a slow-release form. Suitable dosage forms are described in Examples 10 and 11.

EXAMPLE 7

Oral Slow-release Tablet

A granulate is prepared having the following composition (per tablet): Pyridoxal.HCl 12.12 mg, emcompress (insoluble dicalcium phosphate filler) 125 mg, 5% gelatine sol. q.s. The granules are mixed with (per tablet) 125 mg 0 emcompress, Natrosol (hydroxy ethyl cellulose) 125 mg, magnesium stearate 6.3 mg, and further 5% gelatine gel 9.5, mixed in a turbulo mixer and pressed into tablets.

EXAMPLE 8

Example 7 is repeated, using pyridoxamine. HCl instead of pyridoxal.HCl.

EXAMPLE 9

Pyridoxal-fortified Additive for Use in Infant Foods

A pyridoxal-fortified additive is formulated as follows:

| | |
|---|---|
| Pyridoxal.HCl | 10.0 mg |
| Homogenized powdered milk | 100 g |

The additive may be added to any infant feed formula (preferably of the humanized type) on the basis of 1.0 g of additive per kg bodyweight per day.

EXAMPLE 10

Pyridoxal-fortified Infant Food Formula

A basic infant food formula is composed in the usual manner containing powdered homogenized milk powder with added lactose, coconut and corn oil, and sodium citrate such that the composition is as follows:

Protein 1.6%; fat 3.3%; carbohydrate 67.0%.

The following quantifies of vitamin and minerals are added per 20 g of this product:

| | |
|---|---|
| Pyridoxal.HCl | 0.08 mg |
| Vitamin A | 50 IU |
| Vitamin C | 4.0 mg |
| Vitamin D2 | 50 IU |
| Vitamin E | 0.5 mg ($\alpha$-tocopherol) |
| Vitamin B1 | 0.06 mg |
| Vitamin B2 | 0.07 mg |
| Vitamin B12 | 0.17 mg |
| Niacin | 1.0 mg |
| Ca pantothenate | 0.3 mg |
| Folic acid | 0.5 mg |
| Pyridoxine.HCl | 0.02 mg |
| Citric acid | 0.013 |
| Iron (as Fe fumarate) | 2.0 mg |
| Calcium (as calcium gluconate) | 10 mg |
| Magnesium (as Mg ascorbate) | 5 mg |
| Zinc (as Zn gluconate) | 0.2 mg |
| Iodide (as KI) | 7.0 mg |

Before use, 3.0 g are dissolved in 25 ml of water. 60–150 ml per kg bodyweight are given to premature infants during the first few days of life, with subsequent appropriate increases and adaptations.

EXAMPLE 11

Pyridoxal-containing Paediatric Syrup

Composition per ml:

| | |
|---|---|
| Vitamin A | 50 IU |
| Vitamin B1 | 0.06 mg |
| Vitamin B2 | 0.07 mg |
| Pyridoxal hydrochloride | 0.08 mg |
| Pyridoxine hydrochloride | 0.02 mg |
| Glycine | 0.1 g |
| Vitamin B12 | 0.17 micrograms |
| Propylene glycol | 0.1 g |
| Nicotinamide | 1.0 mg |
| Vitamin C | 4.0 mg |
| Vitamin D2 | 50 IU |
| Pantothenic acid | 0.3 mg |
| Citric acid | 0.013 mg |
| Iron (as Fe fumarate) | 2.0 mg ($Fe^{++}$) |
| Calcium (as Ca gluconate) | 60 mg |
| Magnesium (as Mg ascorbate) | 8 mg |
| Zinc (as Zinc gluconate) | 0.5 mg |
| Potassium iodide | 7.3 mg |
| Lysine hydrochloride | 1.5 mg |
| Chorine chloride | 0.5 mg |
| $\alpha$-Tocopherol | 0.5 mg |
| Folic acid | 5.0 micrograms |
| Sodium saccharin | 2 mg |
| Sodium cyclamate | 10 mg |
| Keltrol F | 2 mg |
| Excipients | 25 mg |

1.0 ml/kg bodyweight is administered daily.

EXAMPLE 12

To confirm the inability of immature calls to convert pyridoxine into pyridoxal and its phosphate, an aspirate of bone marrow was tested. It was incapable of convening pyridoxine into pyridoxal, demonstrating the absence of adequate oxidase activity in premature red blood cells.

EXAMPLE 13

Pediatric Tablets 3 types of tablets are prepared having the following compositions:

| | Per tablet (A) | Per tablet (B) | Per tablet (C) |
|---|---|---|---|
| PL | 0.21 mg | 0.10 | 0.04 |
| PN | 0.06 mg | 0.03 | 0.012 |
| Riboflavin | 0.24 mg | 0.12 | 0.05 |
| Anhydrous lactose | q.s. (30–40 mg) | | |
| Daily dose: | Tablets A: 1 tablet | | |
| | Tablets B: 2 tablets | | |
| | Tablets C: 5 tablets | | |

The soluble tablets are added in accordance with the daily supplement regimen to a conventional feed formula.

EXAMPLES 14 to 16

These are suitably formulated as sterilised solutions having the compositions indicated (per 1000 ml of solution). In all cases due provision is made for osmolality requirements by addition of NaCl or by dilution.

The compositions given below may also be provided in powdered form (in the proportions indicated) in sterile ampoules or other containers, for dissolution in sterile water and dilution to a prescribed volume immediately before use..

EXAMPLE 14

General Solution for Intravenous Administration

| | Range | Preferred range | Preferred |
|---|---|---|---|
| (a) | | | |
| Pyridoxal.HCl* | 2–1000 mg | 20–100 mg | 50 mg |
| Glucose | 1–100 g | 20–80 mg | 50 g |
| $ZnCl_2$ | 1–1000 mg | 5–15 mg | 10 mg |
| Ascorbic acid | 1–5000 mg | 50–500 mg | 100 mg |
| (b) | | | |
| Pyridoxal.HCl* | 2–500 mg | 20–300 mg | 100 mg |
| $ZnCl_2$ | 1–1000 mg | 5–15 mg | 10 mg |
| Ascorbic acid | 1–5000 mg | 50–500 mg | 100 mg |

*May be varied as desired to provide for an infusion rate per hour of PL of 5 to g (preferred 50 mg) in humans.

Infusion rates (in both cases) using the compositions according to the last column: 50 to 150 ml/h

EXAMPLE 15

Solution for the Treatment of Shock a) Ringer's lactate solution
  NaCl=6.0 g; Sodium lactate=3.2 g;
  KCl=400 mg; $CaCl.H_2O$=270 mg;
  Pyddoxal. HCl*=1 to 1000 mg (preferred range: 20 to 200 mg; preferred: 100 mg.
  *May be varied as desired to provide for an infusion rate per hour of PL of 5–500 mg (preferred 50 mg).) in humans;
  Zinc chloride=1 to 1000 mg (preferred range: 5 to 15 mg; preferred: 10 mg);

Ascorbic acid=1 to 5000 mg (preferred range: 50 to 500 mg; preferred: 100 mg).

This solution contains electrolytes in mmol/l as follows: Na=131, K=5, Ca=2, Cl=111, lactate as $HCO_3$=29, and has milliosmol/l of about 279 and pH of about 6.5.

b) Electrolyte solution

NaCl=6.0 g; $NaHCO_3$=2.3 g;
KCl=300 mg; $MgCl_2.6H_2O$=300 mg;
Pyridoxal. HCl*=1 to 1000 mg (preferred range: 20 to 200 mg; preferred: 100 mg.

*May be varied as desired to provide for an infusion rate per hour of PL 20 of 5–500 mg (preferred 50 mg).) in humans;

$ZnCl_2$=1 to 1000 mg (preferred range: 5 to 15 mg; preferred: 10 MG);

Ascorbic acid=1 to 5000 mg (preferred range: 50 to 500 mg; preferred: 100 mg).

Rate of infusion: 1.0 to 1.5 ml/kg/h.

This solution contains electrolytes in mmol/l as follows: Na=130, K=4, Mg=1.5, Cl=109, $HCO_3$=28 and has milliosmol/l of 273 and pH of 7.4.

EXAMPLE 16

Solution for Intravenous Infusion

|  | Range | Preferred Range | Preferred |
|---|---|---|---|
| Pyridoxal.HCl* | 2–1000 mg | 20–100 mg | 50 mg |
| Pyridoxine.HCl | 1–1000 mg | 2–20 mg | 5 mg |
| Glucose | 1–100 g | 20–80 g | 50 g |
| Glutamate | 1–500 mg | 4–200 mg | 100 mg |
| $ZnCl_2$ | 1–500 mg | 5–15 mg | 10 mg |
| $MgCl_2$ | 5–5000 mg | 100–500 mg | 399 mg |
| Riboflavine | 1–100 mg | 5–20 mg | 10 mg |
| Ascorbic acid | 1–5000 mg | 50–500 mg | 100 mg |
| NaCl | (as required) | | |

*May be varied as desired to provide for an infusion rate per hour of PL of 5 to 500 mg (preferred 50 mg) in humans.

Preferred rate of infusion: 1.0 to 1.5 ml/kg/h.

EXAMPLE 17

Per os (one daily dose)

| PL | 10–500 mg, e.g. 200 mg |
|---|---|
| PN | 10–500 mg, e.g. 200 mg |
| Riboflavine | 1–100 mg, e.g. 10 mg |
| $ZnCl_2$ | 1–100 mg, e.g. 50 mg |
| $MgCl_2$ | 1–5000 mg, e.g. 2000 mg |
| Ascorbic acid | 100 mg |

Given as a solution or in the form of tablets or capsules, preferably in a slow release formulation.

EXAMPLE 18

Suppositories

| PL | 10–500 mg, e.g. 200 mg |
|---|---|
| PN | 10–500 mg, e.g. 200 mg |
| Riboflavine | 1–100 mg, e.g. 10 mg |
| $ZnCl_2$ | 1–50 mg, e.g. 20 mg |
| $MgCl_2$ | 1–2000 mg, e.g. 1000 mg |
| Ascorbic acid | 100 mg |

These ingredients to be included with the usual excipients, carriers, etc. used in the formulation of suppositories.

EXAMPLE 19

Administration of Pyridoxal Containing Infusions to Critically Ill Patients

Composition per liter: NaCl: 6.0 g, $NaHCO_3$:2.3 g, KCl: 300 mg, Mg $Cl_2.6H_2O$: 300 mg, Pyridoxal.HCl: 400 mg.

| Low rate of infusion: | 50 ml/h |
|---|---|
| Intermediary rate of infusion: | 80 ml/h |
| High rate of infusion: | 120 ml/h |

EXAMPLE 20

Cellular Uptake of PL

Fibroblast cell cultures were cultivated in the usual manner in a medium containing different concentrations of various B6 vitamins, and the intracellular PLP content was determined. The results indicated that intracellular PLP levels could be increased by increasing extracellular PN and/or PL concentrations, but that PL was more effective than PN in doing so. Extracellular PLP was not accumulated by the cells. This observation was confirmed by incubating the cells with radioactive PLP: very little radioactivity appeared in the intracellular fraction. When PN was used in the medium, intracellular PLP levels increased much more slowly (and in a time dependent manner) than when PL was used as extracellular source.

When the extracellular PL concentration was 60 nM, intracellular PLP levels reached a concentration of 12 nmol/g cell protein. When extracellular levels were increased, intracellular PLP levels increased correspondingly in an approximately linear fashion until a maximum value of 120 nmol/g cell protein was reached at an extracellular PL concentration of 600 nM. Further increases in intracellular PLP values indicated that cellular PL uptake is a saturable process. Moreover, when both PN and PL were included in the medium, intracellular PLP accumulation was decreased in comparison with PLP accumulation seen when PL alone (in equimolecular concentrations) was included in the medium. This effect was most noticeable in the higher concentration ranges and indicates that high concentrations of PN actually suppress intracellular PLP accumulation.

EXAMPLE 21

Bottle Feed Supplement

Rapidly dissolving tablets were made as follows:
Per tablet

| Pyridoxal (as pyridoxal hydrochloride) | 0.10 mg |
|---|---|
| Pyridoxine (as pyridoxine hydrochloride) | 0.05 mg |
| Riboflavin (as riboflavin phosphate sodium) | 0.10 mg |
| Ascorbic Acid | 25.0 mg |
| Vit E (as d-alpha-tocopherol acetate) | 2.0 mg |
| Folic acid | 0.02 mg |
| Cyanocobalamin | 0.00055 mg |
| Zinc (as zinc citrate) | 2.0 mg |
| Selenium (as selenised yeast) | 5.0 microgram |
| Avicel | 45 mg |
| Magnesium, stearate | 0.05 mg |
| Aerosil | 0.05 mg |

Tablets were prepared in the usual manner. One tablet is added twice daily to the infant's bottle feed immediately before feeding.

Total daily dose: 2 tablets.

The pharmacology and toxicology of all active substances employed in accordance with the present invention is known per se and requires no description. As regards evidence of synergism between these ingredients reference is made to our copending application claiming the priority of South African patent application 92/6990.

Clinical Tests on Infant Formulations

A) The following are results of measurements of the vitamin status in serum of diverse infants. In the table the prefix "S" denotes "Serum".

| BABY | AGE (days) | S-PLP nmol/ml | S-PL nmol/ml | S-PL S-PLP | S-B12 pmol/ml | S FOLATE nmol/ml | S-HC umol/ml |
|---|---|---|---|---|---|---|---|
| MOTHER'S MILK PLUS FORMULA | | | | | | | |
| 1. SR | 2 | 49.8 | 324 | 6.5 | 725 | 45 | 5.1 |
| 2. SM | 14 | 66.1 | 465 | 7.1 | 504 | 31.7 | 3.9 |
| 3. SL | 5 | 38.5 | 48.7 | 1.3 | — | — | 10.8 |
| 4. IS* | 8 | 15.6 | 143.3 | 9.2 | 452 | 26.6 | 6.1 |
| 5. JM* | 20 | 52.3 | 306 | 5.9 | 250 | 45 | 7.3 |
| 6. ME* | 10 | 52.2 | 303 | 5.8 | 478 | 26.9 | 5.7 |
| 7. IK* | 7 | 63 | 167 | 2.7 | 418 | 27.1 | 4.2 |
| 8. KM | 4 | 12.1 | 52.5 | 4.3 | 311 | 45 | 5.1 |
| 9. ML** | 4 | 14.2 | 9.4 | 0.6 | — | — | 6.5 |
| 10. FV | 9 | 129.1 | 309 | 2.4 | 707 | 45 | 7.2 |
| FORMULA only | | | | | | | |
| 11. JB* | 12 | 70 | 464 | 6.6 | 290 | 45 | 8.5 |
| 12. RM | 3 | 32 | 14.4 | 0.4 | 658 | 45 | 6.5 |
| BREAST only | | | | | | | |
| 13. VM | 4 | 44.9 | 17.1 | 0.4 | 225 | 45 | 7.4 |
| HYPERALIMENTATION | | | | | | | |
| 14. EM | 11 | 4.9 | 11.7 | 2.4 | 541 | 28.4 | 4.7 |

*Premature birth
**Diabetic

B) Blood levels of PL in premature infants receiving feed supplement in accordance with the invention are summarised in the following:

Average Gestational age: 27 weeks

Two groups, (n=7) each

Both groups were on a normal hospital feeding programme bottle feed for premature infants. The experimental group received additionally two tablets of a rapidly dissolving PL containing tablet according to the invention, (0,1 mgPL/tablet) daily. None received any mothers milk.

Results (average values)

|  | Admission | 2 | 5 | 7 | 14 days |
|---|---|---|---|---|---|
| S-PLP (nmol/l) | | | | | |
| Control | 24* | 11 | 7 | 7.5 | 8 |
| Exp. | 27* | 10 | 9 | 6 | 7 |
| S-PL (nmol/l) | | | | | |
| Control | 190 | 181 | 196 | 191 | 174 |
| Exp | 181 | 196 | 221 | 229 | 246 |

*Immediately after birth: still from mother, rapid drop during first 3 days.

C) For ethical reasons it was not possible to obtain repeated blood samples from infants during comprehensive clinical trials. Reliance is therefore placed on trials performed on human adults as reported in the copending application claiming the priority of South African patent application 92/6990, which show that for humans of all age groups, in order to lower elevated homocysteine levels in plasma (which are frequently paralled by methionine levels) the following was found:

PL supplementation alone: 18.8% success

Vitamin B12 supplementation alone: 31.3% success

Folate supplementation alone: 62.5% success

Combination of all three supplementation alone: 91.7% success after 6 weeks and 100% after 8 weeks.

There was clear evidence of synergism between the three components.

D) Summary of clinical findings

1. In healthy infants plasma PL levels are very much higher than in adults. The ratio of PL:PLP in plasma in infants is approximately 10 or more times as high as in adults. This shows that PL in plasma is of fundamental importance to human infants.

2. Low plasma P/PLP ratios can often be correlated with abnormally high plasma-homocysteine levels in infants.

3. In other infants high plasma-homocysteine levels can be correlated with low serum B12 and/or folate levels.

4. PL supplementation in infants, in particular premature infants increases plasma PL and intracellular PLP levels, but not plasma PLP levels (the latter was also found by Raiten, Reynolds, et al (Am J.Clin. Nutr. 1991; 53:78–83). Plasma PLP is unimportant in infants.

5. Premature infants (gestational age 30 weeks or less) are generally unable to effectively convert PN into PL. The ability to so convert improves (to a highly variable extent) both with gestational age and age after birth, although approximately 20% remain poor converters into adulthood. To compensate for this by prior art high dosage PN supplementation is not possible and produces dangerous side effects.

6. The formula for infants has been confirmed, based on the clinical trials C) on adults, duly adapted in the light of the clinical findings as per A) and B).

I claim:

1. The method of raising the intracellular level, other than in a healthy liver, of pyridoxal (PLP) and the plasma level of pyridoxal (PL) in a human or animal patient having insufficient ability to convert pyridoxine (PN) into intracellular PLP leading to depressed or inadequate intracellular PLP contents, said insufficient activity arising from a condition ranging from depressed to absent enzymatic activity, caused by an inherent cellular defect, otherwise than primary acquired sideroplastic anaemia, which comprises administering to the patient an active agent selected from the group consisting of pyridoxal (PL, pyridoxamine, actals of pyridoxal, condensation products arising from the reaction of the aldehyde group of pyridoxal with an amine and addition salts of any of the foregoing members of the group with pharmaceutically acceptable acids in an amount and at a rate effective to supply from 0.008 to 7.2 mg/kg/day of said source, calculated as pyridoxal and based on body weight.

2. The method as claimed in claim 1 of treating conditions selected from the group consisting of
   a) premature infants for infantile elevated homocysteine and/or methionine levels;
   b) depressed to inadequate intracellular pyridoxal phosphate levels due to cellular immaturity,
   c) deficiencies associated with non-human milk-based diets and infant feed formulae;
   d) depressed to inadequate intracellular pyridoxal phosphate levels in a patient resulting from an enzymatic condition caused by an inherent cellular defect, wherein the pyridoxine PN—intracellular pyridoxal phosphate PLP pathway is disturbed;
   e) genetic lack of oxidase;
   f) genetic oxidase polymorphism;
   g) anaemia other than primary acquired sideroplastic anaemia;
   h) depressed level of enzymatically mature erythrocytes;
   i) depressed level of enzymatically intact erythrocytes;
   j) lack of hemoglobin;
   k) a microbial disease which destroys erythrocytes; and
   l) a condition according to a) to l) herein, complicated by a disease causing release of toxins of biogenic polyamines.

3. The method as claimed in claim 2, applied to the treatment of a condition wherein the depressed to absent enzymatic activity is caused by cellular immaturity.

4. The method as claimed in claim 3, applied to the treatment of an infant suffering from intracellular pyridoxal phosphate insufficiency.

5. The method as claimed in claim 4, applied to the treatment of premature infants.

6. The method as claimed in claim 1, wherein in addition at least one substance selected from the group consisting of a source of zinc and a source of magnesium is administered as a potentiator for pyridoxal at a dosage rate of 0.05 to 0.9 mg/kg/day of zinc and 0.5 to 10 mg/kg/day of magnesium.

7. The method as claimed in claim 2, wherein the composition is administered as an infusion.

8. The method as claimed in claim 3, wherein the source is added in the form of a nutritional supplement in dosage units to an infant feed formulation.

9. The method as claimed in claim 8, wherein said source additionally includes PN.

10. The method as claimed in claim 3, applied to the nutritional supplementation of infant diets, the treatment and the prophylaxis of infantile conditions selected from the group consisting of elevated homocysteine levels, methionine levels, and deficiencies associated with diets and infant feed formulae, based on non-human milk.

11. The method of claim 10 which comprises administering, in addition to Vitamin B6 said active agent, a member selected from the group consisting of folic acid and a pharmaceutically acceptable salt thereof and vitamin B12, all within conventional dosage ranges.

12. The method as claimed in claim 10 which comprises administering to an infant a preparation comprising in combination:
   a) the said active agent;
   b) a folate source selected from the group consisting of folate and precursors of folate which release folate in vivo; and
   c) a member of the group consisting of vitamin B12 and vitamin B12 in the presence of intrinsic factor, in the following ratios:
      a):b) from 1:25 to 10 000:1
      b):c) from 1:1 to 50 000:1.

13. The method as claimed in claim 12, wherein said ratios are:

| a):b) | from 2:5 | to 150:1 |
| b):c) | from 2:1 | to 4000:1. |

14. The method as claimed in claim 13, wherein said ratios are approximately:

| a):b) = | 15:2 |
| b):c) = | 400:11 |

15. The method as claimed in claim 13, wherein said administration proceeds by the oral route.

16. The method as claimed in claim 12, which comprises the inclusion of a source of PN selected from the group consisting of PN and PN precursors in the preparation in addition to the aforesaid source of vitamin B6 in a ratio calculated as PN:PL in the range 10:1 to 1:10.

17. The method as claimed in claim 17, wherein the ratio of PN:PL is in the range 4:1 to 1:6.

18. The method as claimed in claim 17, wherein the ratio of PN:PL is from 2:1 to 1:3.

19. The method as claimed in claim 16, wherein the preparation comprises riboflavin in an amount of from 0.5 to 5 times the mount of PN.

20. The method as claimed in claim 12, wherein the preparation in addition comprises an antioxidant.

21. The method as claimed in claim 20, wherein said antioxidant is selected from the group consisting of one or more of d) vitamin C, e) vitamin E and f) selenium, said antioxidant being present in amounts providing daily dosages:
   d) 10–100 mg
   e) 0.1–20 mg
   f) 1–80 µg.

22. The method as claimed in claim 12, wherein the preparation comprises gamma linolenic acid (LA) to provide a daily dosage of 2–20 mg.

23. The method as claimed in claim 12, wherein the preparation also contains zinc proportioned to provide daily dosages in the range of 0.1–20 mg.

24. The method as claimed in claim 12, wherein the preparation also contains an allergy suppressing substance.

25. The method as claimed in claim 12, wherein the preparation also contains an allergy suppressing substance, derived from substances selected from the group consisting of the herb tea plant *Aspalatus contaminatus* Druce and related species suitable for that purpose.

26. The method as claimed in claim 3 wherein the source of PL is at least one member selected from the group consisting of PL itself, complexes of PL, condensation products arising from the reaction of the aldehyde group of PL with an amine, acetals of PL and addition salts of any of the aforegoing members of the group with pharmaceutically acceptable acids; and mixtures thereof.

27. The method as claimed in claim 26, wherein said source is selected from the group consisting of PL and an acid addition salt of PL.

28. The method according to claim 2, wherein a route of administration is selected from the group consisting of intravenous, intramuscular/subcutaneous and oral.

29. The method according to claim 28, wherein said route of administration is intravenous, and said administration delivers a daily intake rate of 0.01 to 4.2 mg of pyridoxal per kg of body weight.

30. The method according to claim 28, wherein said route of administration is intramuscular, and said administration delivers s a daily intake rate of 0.04 to 7.2 mg of pyridoxal per kg of body weight.

31. The method according to claim 28, wherein said route of administration is oral, and said administration delivers a daily intake rate of 0.03 to 7.2 mg pyridoxal per kg of body weight.

32. The method according to claim 31, wherein said formulation is administered with an infant feed formulation.

33. The method as claimed in claim 2, wherein the composition is administered in a sustained, slow-release galenic form.

34. The method as claimed in claim 3, wherein said source is administered incorporated in an infant feed formulation.

35. The method as claimed in claim 34, wherein said source additionally includes PN.

36. The method as claimed in claim 34, wherein said infant feed formulation is a bottle feed formulation.

37. The method as claimed in claim 12, wherein said preparation is in the form of paediatric drops.

38. The method as claimed in claim 12, wherein said preparation is galenically prepared for parenteral use.

39. The method as claimed in claim 12, wherein said preparation is galenically prepared for infusion.

40. The method as claimed in claim 12, wherein said preparation is galenically prepared as a supplement for addition to an infant feed preparation.

41. The method as claimed in claim 12, wherein said preparation is administered incorporated in an infant feed formulation.

42. The method according to claim 28, wherein said route of administration is subcutaneous, and said administration delivers a daily intake rate of 0.04 to 7.2 mg of pyridoxal per kg of body weight.

43. The method as claimed in claim 3, wherein the composition is itself an infant formulation containing the said pyridoxal or precursor in the required concentration for oral administration.

* * * * *